US005723594A

United States Patent [19]
Janjic et al.

[11] Patent Number: 5,723,594
[45] Date of Patent: Mar. 3, 1998

[54] HIGH AFFINITY PDGF NUCLEIC ACID LIGANDS

[75] Inventors: Nebojsa Janjic; Larry Gold, both of Boulder, Colo.

[73] Assignee: NeXstar Pharmaceuticals, Inc., Boulder, Colo.

[21] Appl. No.: 618,693

[22] Filed: Mar. 20, 1996

Related U.S. Application Data

[63] Continuation-in-part of Ser. No. 479,783, Jun. 7, 1995.

[51] Int. Cl.$^6$ .......................... C07H 21/04; C07H 21/02; C12Q 1/68; C12P 19/34
[52] U.S. Cl. ..................... 536/23.1; 435/6; 435/91.2; 536/25.4; 935/77; 935/78
[58] Field of Search .................. 536/23.1, 25.4; 435/6, 91.2; 935/77, 78

[56] References Cited

U.S. PATENT DOCUMENTS

| | | | |
|---|---|---|---|
| 4,683,195 | 7/1987 | Mullis et al. | 435/6 |
| 4,711,955 | 12/1987 | Ward et al. | 435/6 |
| 4,828,979 | 5/1989 | Klevan et al. | 435/6 |
| 4,935,363 | 6/1990 | Brown et al. | 435/6 |
| 5,070,010 | 12/1991 | Hsu et al. | 435/6 |
| 5,270,163 | 12/1993 | Gold et al. | 435/6 |
| 5,475,096 | 12/1995 | Gold et al. | 435/6 |
| 5,476,766 | 12/1995 | Gold et al. | 435/6 |

FOREIGN PATENT DOCUMENTS

| | | |
|---|---|---|
| 2 183 661 | 6/1987 | United Kingdom . |
| WO/89/06694 | 7/1989 | WIPO . |
| WO/91/19813 | 6/1991 | WIPO . |
| WO/92/05285 | 4/1992 | WIPO . |
| WO/92/14843 | 9/1992 | WIPO . |

OTHER PUBLICATIONS

Johnsson, et al., *Proc. Natl. Acad. Sci., U.S.A.*, 82:1721 (1985).
Ferns, et al., *Science*, 253:1129 (1991).
Herren, et al., *Biochimica et Biophysica Acta*, 1173:294 (1993).
Duan, et al., *J. Biol. Chem.*, 266:413 (1991).
Teisman, et al., *J. Biol. Chem.*, 268:9621 (1993).
Williams, et al., *J. Biol. Chem.*, 259:5287 (1984).
Betsholtz, et al., *Cell*, 39:447 (1984).
Vassbotn, *J. Biol. Chem.*, 267:15635 (1992).
Engstrom, *J. Biol. Chem.*, 267:16581 (1992).
Buchdunger, et al., *Proc. Natl. Acad. Sci., U.S.A.*, 92:2558 (1995).
Kovalenko, et al. *Cancer Res.*, 54:6106 (1994).
Joyce, *Gene*, 82:83 (1989).
Joyce and Inoue, *Nucleic Acids Research*, 17:711 (1989).
Ellington, et al., *Abstract of Papers presented at the 1990 meeting on RNA Processing*, Cold Spring Harbor Laboratory, Cold Spring Harbor, N.Y., p. 226 (1990).
Kinzler, et al. *Nucleic Acids Research*, 17:3645 (1989).
Kramer, et al. *J. Mol. Biol.*, 89:719 (1974).
Levisohn, et al. *Proc. Natl. Acad. Sci.*, USA 63:805 (1969).
Levisohn, et al. *Proc. Natl. Acad. Sci.*, USA60:866 (1968).
Oliphant, et al. *Mol. Cell. Biol.*, 9:2944 (1989).
Oliphant, et al. *Nucleic Acids Research*, 16:7673 (1988).
Oliphant, et al. *Methods in Enzymology*, 155:568 (1987).
Oliphant, et al. *Gene*, 44:177 (1986).
Robertson, et al. *Nature*, 344:467 (1990).
Thiesen, et al. *Nucleic Acids Research*, 18:3203 (1990).
Orgel, *Proc. R. Soc. Lond.*, B205:435 (1979).
Bass, et al. *Nature*, 308:820 (1984).
Carey, et al. *Biochemistry*, 22:2601 (1983).
Joyce, *RNA: Catalysis, Splicing, Evolution*, Belfort and Shub (eds.), Elsevier, Amsterdam pp. 83–87 (1989).
Kacian, et al., *Proc. Natl. Acad. Sci. USA*, 69:3038 (1972).
Mills, et al., *Science*, 180:916 (1973).
Mills, et al., *Proc. Natl. Acad. Sci. USA*, 58:217 (1967).
Rich, et al., *Ann. Rev. Biochem*, 53:791 (1984).
Robertson, et al., *Nature*, 344:467 (1990).
Romaniuk, et al., *Biochemistry*, 26:1563 (1987).
Saffhill, et al., *J. Mol. Biol.*, 51:531 (1970).
Schimmel, et al., *Cell*, 58:9 (1989).
Tuerk, et al., *Proc. Natl. Acad. Sci. USA*, 85:1364 (1988).
Uhlenbeck, et al., *J. Biomol. Structure and Dynamics*, 1:539 (1983).
Witherell, et al., *Biochemistry*, 28:71 (1989).
Yarus, *Science*, 240:1751 (1988).
Matthew, et al., *Analytical Biochemistry*, 169:1 (1988).
Andrake, et al., *Proc. Natl. Acad. Sci. USA*, 85:7924 (1988).
Cohen, et al., *Proc. Natl. Acad. Sci. USA*, 63:458 (1969).
Maniatis, et al., *Molec. Cloning: A Laboratory Manual*, Cold Spring Harbor, NY, p. 118 (1982).
Muesing, et al., *Nature*, 313:450 (1985).
Maniatis, et al., *Science*, 236:1237 (1987).
Watson, et al., *Molec. Biol. of the Gene*, Benjamin/Cummings Publishing Co., pp. 267, 295, 323, 361, 394, 396, 397, 405 (1987).
Ma, et al., *Cell*, 51:113 (1987).
Min, et al., *Nucl. Acids Res.*, 16:5075 (1988).
Ou, et al., *Science*, 239:295 (Jan. 15, 1988).
Lestienne, et al., *Biochimie*, 65:49 (1983).
Ellington, et al., *Nature*, 346:818 (1990).
Bock, et al., *Nature*, 355:564 (Feb. 6, 1992).
Stein, et al., *Science*, 261:1004 (Aug. 20, 1993).
Miele, et al., *J. Mol. Biol.*, 171:281–295.
Tuerk, et al., *Science*, 249:505 (1990).

*Primary Examiner*—Stephanie W. Zitomer
*Attorney, Agent, or Firm*—Swanson & Bratschun LLC

[57] ABSTRACT

Methods are described for the identification and preparation of high-affinity nucleic acid ligands to PDGF. Included in the invention are specific ssDNA and RNA ligands to PDGF identified by the SELEX method.

3 Claims, 10 Drawing Sheets

SEQ ID NO: 82

Helix I

SEQ ID NO: 86

$K_d = 0.097$ nM

SEQ ID NO: 87

HIGH AFFINITY PDGF NUCLEIC ACID LIGANDS

RELATED APPLICATIONS

This application is a Continuation-in-Part of U.S. patent application Ser. No. 08/479,783, filed Jun. 7, 1995, entitled High Affinity PDGF Nucleic Acid Ligands.

FIELD OF THE INVENTION

Described herein are methods for identifying and preparing high-affinity nucleic acid ligands to PDGF. The method utilized herein for identifying such nucleic acid ligands is called SELEX, an acronym for Systematic Evolution of Ligands by EXponential enrichment. This invention includes high affinity nucleic acid ligands of PDGF. Further disclosed are ssDNA and RNA ligands to PDGF. The oligonucleotides of the present invention are useful as pharmaceuticals or diagnostic agents.

BACKGROUND OF THE INVENTION

Platelet-derived growth factor (PDGF) was originally isolated from platelet lysates and identified as the major growth-promoting activity present in serum but not in plasma. Two homologous PDGF isoforms have been identified, PDGF A and B, which are encoded by separate genes (on chromosomes 7 and 22). The most abundant species from platelets is the AB heterodimer, although all three possible dimers (AA, AB and BB) occur naturally. Following translation, PDGF dimers are processed into ≈30 kDa secreted proteins. Two cell surface proteins that bind PDGF with high affinity have been identified, $\alpha$ and $\beta$ (Heldin et al., *Proc. Natl. Acad. Sci.*, 78: 3664 (1981); Williams et al., *Proc. Natl. Acad. Sci.*, 79: 5867 (1981)). Both species contain five immunoglobulin-like extracellular domains, a single transmembrane domain and an intracellular tyrosine kinase domain separated by a kinase insert domain. The functional high affinity receptor is a dimer and engagement of the extracellular domain of the receptor by PDGF results in cross-phosphorylation (one receptor tyrosine kinase phosphorylates the other in the dimer) of several tyrosine residues. Receptor phosphorylation leads to a cascade of events that results in the transduction of the mitogenic or chemotactic signal to the nucleus. For example, in the intracellular domain of the PDGF $\beta$ receptor, nine tyrosine residues have been identified that when phosphorylated interact with different src-homology 2 (SH2) domain-containing proteins including phospholipase C-$\gamma$, phosphatidylinositol 3'-kinase, GTPase-activating protein and several adapter molecules like Shc, Grb2 and Nck (Heldin, *Cell*, 80: 213 (1995)). In the last several years, the specificities of the three PDGF isoforms for the three receptor dimers ($\alpha\alpha$, $\alpha\beta$, and $\beta\beta$) has been elucidated. The $\alpha$-receptor homodimer binds all three PDGF isoforms with high affinity, the $\beta$-receptor homodimer binds only PDGF BB with high affinity and PDGF AB with approximately 10-fold lower affinity, and the $\alpha\beta$-receptor heterodimer binds PDGF BB and PDGF AB with high affinity (Westermark & Heldin, *Acta Oncologica*, 32: 101 (1993)). The specificity pattern results from the ability of the A-chain to bind only to the $\alpha$-receptor and of the $\beta$-chain to bind to both $\alpha$ and B-receptor subunits with high affinity.

The earliest indication that PDGF expression is linked to malignant transformation came with the finding that the amino acid sequence of PDGF-B chain is virtually identical to that of p28$^{sis}$, the transforming protein of the simian sarcoma virus (SSV) (Waterfield et al. *Nature*, 304: 35 (1983); Johnsson et al., *EMBO J.*, 3: 921 (1984)). The transforming potential of the PDGF-B chain gene and, to a lesser extent, the PDGF-A gene was demonstrated soon thereafter (Clarke et al., *Nature*, 308: 464 (1984); Gazit et al., *Cell*, 39: 89 (1984); Beckmann et al., *Science*, 241:1346; Bywater et al., *Mol. Cell. Biol.*, 8: 2753 (1988)). Many tumor cell lines have since been shown to produce and secrete PDGF, some of which also express PDGF receptors (Raines et at., *Peptide Growth Factors and Their Receptors*, Springer-Verlag, Part I, p 173 (1990)). Paracrine and, in some cell lines, autocrine growth stimulation by PDGF is therefore possible. For example, analysis of biopsies from human gliomas has revealed the existence of two autocrine loops: PDGF-B/$\beta$-receptor in tumor-associated endothelial cells and PDGF-A/$\alpha$-receptor in tumor cells (Hermansson et at., *Proc. Natl. Acad. Sci.*, 85: 7748 (1988); Hermansson et al., *Cancer Res.*, 52: 3213 (1992)). The progression to high grade glioma was accompanied by the increase in expression of PDGF-B and the $\beta$-receptor in tumor-associated endothelial cells and PDGF-A in glioma cells. Increased expression of PDGF and/or PDGF receptors has also been observed in other malignancies including fibrosarcoma (Smits et al., *Am. J. Pathol*, 140: 639 (1992)) and thyroid carcinoma (Heldin et at., *Endocrinology*, 129: 2187 (1991)).

In view of its importance in proliferative disease states, antagonists of PDGF may find useful clinical applications. Currently, antibodies to PDGF (Johnsson et al., (1985) *Proc. Natl. Acad. Sci., U.S.A.* 82: 1721–1725; Ferns et al., (1991) *Science* 153: 1129–1132; Herren et al., (1993) *Biochimica et Biophysica Acta* 1173, 194–302) and the soluble PDGF receptors (Herren et al., (1993) *Biochimica et Biophysica Acta* 1173: 194–302; Duan et al., (1991) *J. Biol. Chem.* 266: 413–418; Teisman et al., (1993) *J. Biol. Chem.* 268: 9621–9628) are the most potent and specific antagonists of PDGF. Neutralizing antibodies to PDGF have been shown to revert the SSV-transformed phenotype (Johnsson et al., (1985) *Proc. Natl. Acad. Sci., U.S.A.* 82: 1721–1725) and to inhibit the development of neointimal lesions following arterial injury (Ferns et al., (1991) *Science* 153:1129–1132). Other inhibitors of PDGF such as suramin (Williams et al., (1984) *J. Biol. Chem.* 259: 5287–5294; Betsholtz et al., (1984) *Cell* 39 447–457), neomycin (Vassbotn et al., (1992) *J. Biol. Chem.* 267 15635–15641) and peptides derived from the PDGF amino acid sequence (Engström et al.., 1992) *J. Biol. Chem.* 267: 16581–16587) have been reported, however, they are either too toxic or lack sufficient specificity or potency to be good drug candidates. Other types of antagonists of possible clinical utility are molecules that selectively inhibit the PDGF receptor tyrosine kinase (Buchdunger et at., (1995) *Proc. Natl. Acad. Sci., U.S.A.* 92: 2558–2562; Kovalenk et al., (1994) *Cancer Res.* 54: 6106–6114).

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled "Nucleic Acid Ligands," now U.S. Pat. No. 5,270,163 (see also WO91/19813), each of which is herein specifically incorporated by reference. Each of these applications, collectively referred to herein as the SELEX patent applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat No. 5,580,737 describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," describes a SELEX-based method which achieves highly efficient partitioning between oligonucleotides having high and low affinity for a target molecule. U.S. patent application Ser. No. 07/964, 624, filed Oct. 21, 1992, entitled "Methods of Producing Nucleic Acid Ligands" now U.S. Pat. No. 5,496,938 describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," that describes oligonucleotides containing nucleotide derivatives chemically modified at the 5-and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

In the present invention, the identification of high-affinity nucleic acid ligands to PDGF is described. Specifically, single stranded DNA ligands and 2'-fluoropyrimidine RNA ligands to PDGF are described. Furthermore, a consensus secondary structure motif is described.

BRIEF SUMMARY OF THE INVENTION

The present invention includes methods of identifying and producing nucleic acid ligands to platelet-derived growth factor (PDGF) and homologous proteins and the nucleic acid ligands so identified and produced. For the purposes of this application, PDGF refers to PDGF AA, AB, and BB isoforms and homologous proteins. Specifically included in the definition are human PDGF AA, AB, and BB isoforms. Specifically included in the invention are the ssDNA ligand sequences shown in Tables 2 and 3 and FIGS. 1, 2 and 8 (SEQ ID NOS:4–35). Further included in the invention are the RNA ligand sequences shown in Table 7 (SEQ ID NOS:39–81).

Further included in this invention is a method of identifying nucleic acid ligands and nucleic acid ligand sequences to PDGF comprising the steps of (a) preparing a candidate mixture of nucleic acids, (b) contacting the candidate mixture of nucleic acids with PDGF, (c) partitioning between members of said candidate mixture on the basis of affinity to PDGF, and (d) amplifying the selected molecules to yield a mixture of nucleic acids enriched for nucleic acid sequences with a relatively higher affinity for binding to PDGF.

More specifically, the present invention includes the ssDNA and RNA ligands to PDGF identified according to the above-described method, including those ligands shown in Tables 2, 3, and 7, and FIGS. 1, 2, and 8 (SEQ ID NOS:4–35; 39–81). Also included are DNA and RNA ligands to PDGF that are substantially homologous to any of the given ligands and that have substantially the same ability to bind PDGF. Further included in this invention are nucleic acid ligands to PDGF that have substantially the same structural form as the ligands presented herein and that have substantially the same ability to bind PDGF.

The present invention also includes modified nucleotide sequences based on the ssDNA and RNA ligands identified herein and mixtures of the same.

BRIEF DESCRIPTION OF THE FIGURES

FIG. 2 shows the minimal ligands 20t, 36t and 41t folded according to the consensus secondary structure motif. [3'T] represents a 3'-3' linked thymidine nucleotide added to reduce 3'-exonuclease degradation.

DETAILED DESCRIPTION OF THE INVENTION

Figure 1:
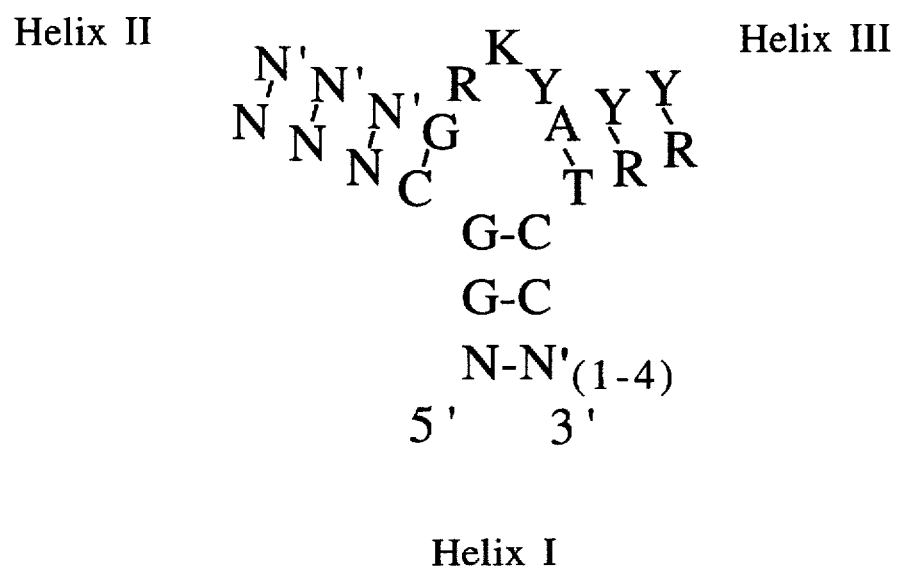
FIG. 1 shows the consensus secondary structure for the sequence set shown in Table 3. R=A or G, Y=C or T, K=G or T, N and N' indicate any base pair.

This application describes high-affinity nucleic acid ligands to PDGF identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096 U.S. patent application Ser. No. 07/931,473, filed Aug. 17, 1992, entitled Nucleic Acid Ligands, now U.S. Pat. No. 5,270,163, (see also WO91/19813). These applications, each specifically incorporated herein by reference, are collectively called the SELEX patent applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX patent applications describe and elaborate on this process in great detail. Included are targets that can be used in the process; methods for partitioning nucleic acids within a candidate mixture; and methods for amplifying partitioned nucleic acids to generate enriched candidate mixture. The SELEX patent applications also describe ligands obtained to a number of target species, including both protein targets where the protein is and is not a nucleic acid binding protein.

The nucleic acid ligands described herein can be complexed with a lipophilic compound (e.g., cholesterol) or attached to or encapsulated in a complex comprised of lipophilic components (e.g., a liposome). The complexed nucleic acid ligands can enhance the cellular uptake of the nucleic acid ligands by a cell for delivery of the nucleic acid ligands to an intracellular target. U.S. patent application Ser. No. 08/434,465, filed May 4, 1995, entitled "Nucleic Acid Ligand Complexes," which is incorporated in its entirety herein, describes a method for preparing a therapeutic or diagnostic complex comprised of a nucleic acid ligand and a lipophilic compound or a non-immunogenic, high molecular weight compound.

The methods described herein and the nucleic acid ligands identified by such methods are useful for both therapeutic and diagnostic purposes. Therapeutic uses include the treatment or prevention of diseases or medical conditions in human patients. Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to PDGF described herein may specifically be used for identification of the PDGF protein.

SELEX provides high affinity ligands of a target molecule. This represents a singular achievement that is unprecedented in the field of nucleic acids research. The present invention applies the SELEX procedure to the specific target of PDGF. In the Example section below, the experimental parameters used to isolate and identify the nucleic acid ligands to PDGF are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), now U.S. Pat. No. 5,496,938, methods are described for obtaining improved nucleic acid ligands after SELEX has been performed. The '624 application, entitled Methods of Producing Nucleic Acid Ligands, is specifically incorporated herein by reference. Further included in this patent are methods for determining the three-dimensional structures of nucleic acid ligands. Such methods include mathematical modeling and structure modifications of the SELEX-derived ligands, such as chemical modification and nucleotide substitution.

In the present invention, two SELEX experiments were performed in order to identify ssDNA and RNA with specific high affinity for PDGF from degenerate libraries containing 40 and 50 random positions (40N SEQ ID NO:1 and 50N SEQ ID NO:36), respectively (Tables 1 and 6). This invention includes the specific ssDNA and RNA ligands to PDGF shown in Tables 2, 3 and 7 and FIGS. 1, 2, and 8 (SEQ ID NOS:4–35; 39–87), identified by the methods described in Examples 1 and 3. The scope of the ligands covered by this invention extends to all nucleic acid ligands of PDGF, modified and unmodified, preferably those identified according to the SELEX procedure. More specifically, this invention includes nucleic acid sequences that are substantially homologous to the ligands shown in Tables 2, 3 and 7 and FIGS. 1, 2, and 8 (SEQ ID NOS:4–35; 39–81). By substantially homologous it is meant a degree of primary sequence homology in excess of 70%, most preferably in excess of 80%. A review of the sequence homologies of the ligands of PDGF shown in Tables 2 and 7 (SEQ ID NOS:4–35; 39–81) shows that sequences with little or no primary homology may have substantially the same ability to bind PDGF. For these reasons, this invention also includes nucleic acid ligands that have substantially the same structure and ability to bind PDGF as the nucleic acid ligands shown in Tables 2, 3 and 7 and FIGS. 1, 2, and 8 (SEQ ID NOS:4–35; 39–87). Substantially the same structure includes all nucleic acid ligands having the common structural elements shown in FIG. 1 that lead to the affinity to PDGF. Substantially the same ability to bind PDGF means that the affinity is within one or two orders of magnitude of the affinity of the ligands described herein. It is well within the skill of those of ordinary skill in the art to determine whether a given sequence—substantially homologous to those specifically described herein—has substantially the same ability to bind PDGF.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 9, 1993, entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process.

As described above, because of their ability to selectively bind PDGF, the nucleic acid ligands to PDGF described herein are useful as pharmaceuticals. This invention, therefore, also includes a method for treating PDGF-mediated diseases by administration of a nucleic acid ligand capable of binding to PDGF.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Example 1 describes the various materials and experimental procedures used in evolving ssDNA ligands to PDGF described in Example 2. Example 2 describes the ssDNA ligands to PDGF, the predicted secondary structure of selected nucleic acid ligands, the minimal sequence necessary for high affinity binding, the sites on the nucleic acid ligands and PDGF that are in contact, inhibition by DNA ligands of PDGF isoforms on cultured cells, and inhibition of the mitogenic effects of PDGF in cells by DNA ligands, and substitutions with modified nucleotides. Example 3 describes the experimental procedures used in evolving RNA ligands to PDGF and shows the ligand sequences.

EXAMPLE 1

EXPERIMENTAL PROCEDURES

MATERIALS Recombinant human PDGF-AA (Mr=29,000), PDGF-AB (Mr=27,000) and PDGF-BB (Mr=25,000) were purchased from R&D Systems (Minneapolis, Minn.) in lyophilized form, free from carrier protein. All three isoforms were produced in *E. Coli* from synthetic genes based on the sequences for the long form of the mature human PDGF A-chain (Betsholtz et al., (1986) *Nature* 320: 695-699) and the naturally occurring mature form of human PDGF B-chain (Johnsson et al., (1984) *EMBO J.* 3: 921-928). Randomized DNA libraries, PCR primers and DNA ligands and 5'-iodo-2'-deoxyuridine-substituted DNA ligands were synthesized by NeXstar Pharmaceuticals, Inc. (Boulder, Colo.) or by Operon Technologies (Alameda, Calif.) using the standard solid phase phosphoramidite method (Sinha et al., (1984) *Nucleic Acids Res.* 12: 4539-4557).

SINGLE STRANDED DNA (SSDNA) SELEX

Essential features of the SELEX procedure have been described in detail in the SELEX patent applications (see also Tuerk and Gold, *Science*, 249: 505 (1990); Jellinek et al., *Biochemistry*, 33: 10450 (1994); Jellinek et at., *Proc. Natl. Acad. Sci.*, 90: 11227 (1993), which are incorporated by reference herein. The initial ssDNA library containing a contiguous randomized region of forty nucleotides, flanked by primer annealing regions (Table 1) (SEQ ID NOS:1-3) of invariant sequence, was synthesized by the solid phase phosphoramidite method using equal molar mixture of the four phosphoramidites to generate the randomized positions. The ssDNA library was purified by electrophoresis on an 8% polyacrylamide/7M urea gel. The band that corresponds to the full-length DNA was visualized under UV light, excised from the gel, eluted by the crush and soak method, ethanol precipitated and pelleted by centrifugation. The pellet was dried under vacuum and resuspended in phosphate buffered saline supplemented with 1 mM $MgCl_2$ (PBSM=10.1 mM $Na_2HPO_4$, 1.8 mM $KH_2PO_4$, 137 mM NaCl and 2.7 mM KCl mM $MgCl_2$, pH 7.4) buffer. Prior to incubation with the protein, the ssDNA was heated at 90° C. for 2 minutes in PBSM and cooled on ice. The first selection was initiated by incubating approximately 500 pmol ($3 \times 10^{14}$ molecules) of $5'^{32}P$ end-labeled random ssDNA with PDGF-AB in binding buffer (PBSM containing 0.01% human serum albumin (HSA)). The mixture was incubated at 4° C. overnight, followed by a brief (15 min) incubation at 37° C. The DNA bound to PDGF-AB was separated from unbound DNA by electrophoresis on an 8% polyacrylamide gel (1:30 bis-acrylamide:acrylamide) at 4° C. and at 5 V/cm with 89 mM Tris-borate (pH 8.3) containing 2 mM EDTA as the running buffer. The band that corresponds to the PDGF-ssDNA complex, which runs with about half the electrophoretic mobility of the free ssDNA, was visualized by autoradiography, excised from the gel and eluted by the crush and soak method. In subsequent affinity selections, the ssDNA was incubated with PDGF-AB for 15 minutes at 37° C. in binding buffer and the PDGF-bound ssDNA was separated from the unbound DNA by nitrocellulose filtration, as previously described (Green, et al., (1995) *Chemistry and Biology* 2, 683-695). All affinity-selected ssDNA pools were amplified by PCR in which the DNA was subjected to 12-20 rounds of thermal cycling (30 s at 93° C., 10 s at 52° C., 60 s at 72° C.) in 10 mM Tris-Cl (pH 8.4) containing 50 mM KCl, 7.5 mM $MgCl_2$, 0.05 mg/ml bovine serum albumin, 1 mM deoxynucleoside triphosphates, 5 µM primers (Table 1) (SEQ ID NO:2,3) and 0.1 units/µl Taq polymerase. The 5' PCR primer was 5' end-labeled with polynucleotide kinase and [$\gamma$-$^{32}P$]ATP and the 3' PCR primer was biotinylated at the 5' end using biotin phosphoramidite (Glen Research, Sterling, Va.). Following PCR amplification, streptavidin (Pierce, Rockford, Ill.) was added to the unpurified PCR reaction mixture at a 10-fold molar excess over the biotinylated primer and incubated for 15 min at room temperature. The dsDNA was denatured by adding an equal volume of stop solution (90% formamide, 1% sodium dodecyl sulfate, 0.025% bromophenol blue and xylene cyanol) and incubating for 20 min at room temperature. The radiolabeled strand was separated from the streptavidin-bound biotinylated strand by electrophoresis on 12% polyacrylamide/7M urea gels. The faster migrating radiolabeled (non-biotinylated) ssDNA strand was cut out of the gel and recovered as described above. The mount of ssDNA was estimated from the absorbance at 260 nm using the extinction coefficient of 33 µg/ml/absorbance unit (Sambrook et at., (1989) *Molecular Cloning: A Laboratory Manual*, 2 Ed. 3 vols., Cold Spring Harbor Laboratory Press, Cold Spring Harbor).

Cloning and Sequencing.

The amplified affinity-enriched pool from SELEX round 12 was purified on a 12% polyacrylamide gel and cloned between HindIII and PstI sites in JM109 strain of *E. coli* (Sambrook, et al., (1989) *Molecular Cloning: A Laboratory Manual*, 2 Ed. 3 vols., Cold Spring Harbor Laboratory Press, Cold Spring Harbor). Individual clones were used to prepare plasmids by alkaline lysis. Plasmids were sequenced at the insert region using the forward sequencing primer and Sequenase 2.0 (Amersham, Arlington Heights, Ill.) according to the manufacturer's protocol.

Determination of the apparent equilibrium dissociation constants and the dissociation rate constants The binding of ssDNA ligands at low concentrations to varying concentrations of PDGF was determined by the nitrocellulose filter binding method as described (Green et al., (1995) *Chemistry and Biology* 2: 683-695). The concentrations of PDGF stock solutions (in PBS) were determined from the absorbance readings at 280 nm using the following ε280 values calculated from the amino acid sequences (Gill, S. C., and von Hippel, P. H. (1989) *Anal. Biochem.* 182: 319-326): 19,500 $M^{-1}cm^{-1}$ for PDGF-AA, 15,700 $M^{-1}cm^{-1}$ for PDGF-AB and 11,800 $M^{-1}cm^{-1}$ for PDGF-BB. ssDNA for all binding experiments were purified by electrophoresis on 8% (>80 nucleotides) or 12% (<40 nucleotides) polyacrylamide/7M urea gels. All ssDNA ligands were heated at 90° C. in binding buffer at high dilution (≈1 nM) for 2 min and cooled on ice prior to further dilution into the protein solution. The binding mixtures were typically incubated for 15 min at 37° C. before partitioning on nitrocellulose filters.

The binding of DNA ligands (L) to PDGF-AA (P) is adequately described with the bimolecular binding model for which the fraction of bound DNA at equilibrium (q) is given by eq. 1.

$$q=(f/2[L]_t)\{[P]_t+[L]_t+K_d-[([P]_t+[L]_t+K_d)^2-4[P]_t[L]_t]^{1/2}\} \quad (1)$$

where $[P]_t$ and $[R]_t$ are total protein and total DNA concentrations, $K_d$ is the equilibrium dissociation constant and f is the efficiency of retention of protein-DNA complexes on nitrocellulose filters (Irvine et al., (1991) *J. Mol. Biol.* 222: 739–761; Jellinek et al., (1993) *Proc. Nat'l. Acad. Sci. USA* 90: 11227–11231).

The binding of DNA ligands to PDGF-AB and PDGF-BB is biphasic and can be described by a model in which the DNA ligand is composed of two non-interconverting components ($L_1$ and $L_2$) that bind to the protein with different affinities, described by corresponding dissociation constants, $K_{d1}$ and $Kd_{d2}$ (Jellinek et al., 1993) *Proc. Nat'l. Acad. Sci. USA* 90: 11227–11231). In this case, the explicit solution for the fraction of bound DNA (q) is given by eq. 2.

$$q = f \left( \frac{\chi 1\, K_{d1}}{1+K_{d1}[P]} + \frac{\chi 2\, K_{d2}}{1+k_{d2}[P]} \right)[P]$$

with $$[P] = \frac{[P]_t}{1 + \frac{\chi 1\, K_{d1}[L]_t}{1+K_{d1}[P]} + \frac{\chi 2\, K_{d2}[L]_t}{1+K_{d2}[P]}} \quad (2)$$

where $c_1$ and $c_2(=1-c_1)$ are the mole fractions of $L_1$ and $L_2$. The $K_d$ values for the binding of DNA ligands to PDGF were calculated by fitting the data points to eq. 1 (for PDGF-AA) or eq. 2 (for PDGF-AB and PDGF-BB) using the non-linear least squares method.

The dissociation rate constants ($k_{off}$) were determined by measuring the amount of $^{32}P5'$-end labeled minimal ligands (0.17 nM) bound to PDGF-AB (1 nM) as a function of time following the addition of 500-fold excess of unlabeled ligands, using nitrocellulose filter binding as the partitioning method. The $k_{off}$ values were determined by fitting the data points to the first-order rate equation (eq. 6)

$$(q-q_\infty)/(q_o-q_\infty)=\exp(-k_{off}t) \quad (3)$$

where q, $q_o$ and $q_\infty$ represent the fractions of DNA bound to PDGF-AB at any time (t), t=0 and t=∞, respectively.

Minimal ligand determinations

To generate a population of 5' end-labeled DNA ligands serially truncated from the 3' end, a primer complementary to the 3' invariant sequence region of a DNA ligand template (truncated primer 5N2, Table 1) (SEQ ID NO:3) was radiolabeled at the 5'0 end with [γ-$^{32}$P]-ATP and T4 polynucleotide kinase, annealed to the template and extended with Sequenase (Amersham, Arlington Heights, Ill.) and a mixture of all four dNTPs and ddNTPs. Following incubation in binding buffer for 15 min at 37° C., the fragments from this population that retain high affinity binding to PDGF-AB were separated from those with weaker affinity by nitrocellulose filter partitioning. Electrophoretic resolution of the fragments on 8% polyacrylamide/7M urea gels, before and after affinity selection, allows determination of the 3' boundary. To generate a population of 3' end-labeled DNA ligands serially truncated from the 5' end, the DNA ligands were radiolabeled at the 3' end with [α-$^{32}$P]-cordycepin-5'-triphosphate (New England Nuclear, Boston, Mass.) and T4 RNA ligase (Promega, Madison, Wis.), phosphorylated at the 5' end with ATP and T4 polynucleotide kinase, and partially digested with lambda exonuclease (Gibco BRL, Gaithersburg, Md.). Partial digestion of 10 pmols of 3'-labeled ligand was done in 100 µL volume with 7 mM glycine-KOH (pH 9.4), 2.5 mM MgCl$_2$,1 µg/ml BSA, 15 µg tRNA, and 4 units of lambda exonuclease for 15 min at 37°. The 5' boundary was determined in an analogous manner to that described for the 3' boundary.

Melting temperature ($T_m$) measurements

Melting profiles for the minimal DNA ligands were obtained on a Cary Model 1E spectrophotometer. Oligonucleotides (320–400 nM) were heated to 95° C. in PBS, PBSM or PBS with 1 mM EDTA and cooled to room temperature prior to the melting profile determination. Melting profiles were generated by heating the samples at the rate of 1° C./min from 15°–95° C. and recording the absorbance every 0.1° C. The first derivative of the data points was calculated using the plotting program KaleidaGraph (Synergy Software, Reading, Pa.). The first derivative values were smoothed using a 55 point smoothing function by averaging each point with 27 data points on each side. The peak of the smoothed first derivative curves was used to estimate the $T_m$ values.

Crosslinking of 5-iodo-2'-deoxyuridine-substituted DNA ligands to PDGF-AB

DNA ligands containing single or multiple substitutions of 5'-iodo-2'deoxyuridine for thymidine were synthesized using the solid phase phosphoramidite method. To test for the ability to crosslink, trace amounts of 5'$^{32}$P end-labeled ligands were incubated with PDGF-AB (100 nM) in binding buffer at 37° for 15 min prior to irradiation. The binding mixture was transferred to a 1 cm path length cuvette thermostated at 37° and irradiated at 308 nm for 25–400 s at 20 Hz using a XeCl charged Lumonics Model EX748 excimer laser. The cuvette was positioned 24 cm beyond the focal point of a convergent lens, with the energy at the focal point measuring 175 mjoules/pulse. Following irradiation, aliquots were mixed with an equal volume of formamide loading buffer containing 0.1% SDS and incubated at 95° for 5 min prior to resolution of the crosslinked PDGF/ligand complex from the free ligand on 8% polyacrylamide/7M urea gels.

To identify the protein site of crosslinking for ligand 20t-I4(SEQ ID NO:92), binding and irradiation were done on a larger scale. PDGF-AB and 5' $^{32}$P end-labeled ligand, each at 1 µM in PBSM, were incubated and irradiated (300 s) as described above in two 1 ml reaction vessels. The reaction mixtures were combined, ethanol precipitated and resuspended in 0.3 ml of Tris-HCl buffer (100 mM, pH 8.5). The PDGF-AB/ligand crosslinked complex was digested with 0.17 µg/µl of modified trypsin (Boehringer Mannheim) for 20 hours at 37°. The digest mixture was extracted with phenol/chloroform, chloroform and then ethanol precipitated. The pellet was resuspended in water and an equal volume of formamide loading buffer with 5% (v/v) β-mercaptoethanol (no SDS), incubated at 95° for 5 min, and resolved on a 40 cm 8% polyacrylamide/7M urea gel. The crosslinked tryptic-peptide/ligand that migrated as two closely spaced bands about 1.5 cm above the free ligand band was excised from the gel and eluted by the crush and soak method and ethanol precipitated. The dried crosslinked peptide (about 160 pmoles based on the specific activity)

was sequenced by Edman degradation (Midwest Analytical, Inc., St. Louis, Mo.).

Receptor Binding Assay

The binding of $^{125}$I-PDGF-AA and $^{125}$I-PDGF-BB to porcine aortic endothelial (PAE) cells transfected with PDGF α- or β-receptors were performed as described (Heldin et al., (1988) *EMBO J.* 7, 1387–1394. Different concentrations of DNA ligands were added to the cell culture (1.5 cm$^2$) in 0.2 ml of phosphate buffered saline supplemented with 1 mg bovine serum albumin per ml together with $^{125}$I-PDGF-AA (2 ng, 100,000 cpm) or $^{125}$I-PDGF-BB (2 ng, 100,000 cpm). After incubation at 4° C. for 90 min, the cell cultures were washed and cell associated radioactivity determined in a γ-counter (Heldin et al., (1988) *EMBO J.* 7, 1387–1394).

[$^3$H]thymidine Incorporation Assay

The incorporation of [$^3$H]thymidine into PAE cells expressing PDGF β-receptor in response to 20 ng/ml of PDGF-BB or 10% fetal calf serum and in the presence of different concentrations of DNA ligands was performed as described (Mori et al., (1991) *J. Biol. Chem.* 266, 21158–21164). After incubation for 24 h at 37° C., $^3$H-radioactivity incorporated into DNA was determined using a β-counter.

EXAMPLE 2 ssDNA LIGANDS OF PDGF

High affinity DNA ligands to PDGF AB were identified by the SELEX process from a library of ≈3×10$^{14}$ molecules (500 pmol) of single stranded DNA randomized at forty contiguous positions (Table 1) (SEQ ID NO:1). The PDGF-bound DNA was separated from unbound DNA by polyacrylamide gel electrophoresis in the first round and by nitrocellulose filter binding in the subsequent rounds. After 12 rounds of SELEX, the affinity-enriched pool bound to PDGF-AB with an apparent dissociation constant ($K_d$) of ≈50 pM (data not shown). This represented an improvement in affinity of ≈700-fold compared to the initial randomized DNA library. We used this affinity-enriched pool to generate a cloning library from which 39 isolates were sequenced. Thirty-two of these ligands were found to have unique sequences (Table 2) (SEQ ID NO:4–35). Ligands that were subjected to the minimal sequence determination are marked with an asterisk (*) next to the clone number. The clone numbers that were found to retain high affinity binding as minimal ligands are italicized. All ligands shown in Table 2 were screened for their ability to bind to PDGF AB using the nitrocellulose filter binding method. To identify the best ligands from this group, we determined their relative affinities for PDGF-AB by measuring the fraction of 5' $^{32}$P end-labeled ligands bound to PDGF-AB over a range of protein concentrations. For the ligands that bound to PDGF-AB with high affinity, the affinity toward PDGF-BB and PDGF-AA was also examined: in all cases, the affinity of ligands for PDGF-AB and PDGF-BB was comparable while the affinity for PDGF-AA was considerably lower (data not shown).

Twenty-one of the thirty-two unique ligands can be grouped into a sequence family shown in Table 3(SEQ ID NOS:4, 5, 7–9, 14–24, 26, 31, 32, 34 and 35). The sequences of the initially randomized region (uppercase letters) are aligned according to the consensus three-way helix junction motif. Nucleotides in the sequence-invariant region (lowercase letters) are only shown where they participate in the predicted secondary structure. Several ligands were "disconnected" (equality symbol) in order to show their relatedness to the consensus motif through circular permutation. The nucleotides predicted to participate in base pairing are indicated with underline inverted arrows, with the arrow heads pointing toward the helix junction. The sequences are divided into two groups, A and B, based on the first single stranded nucleotide (from the 5' end) at the helix junction (A or G, between helices II and III). Mismatches in the helical regions are shown with dots under the corresponding letters (G-T and T-G base pairs were allowed). In places where single nucleotide bulges occur, the mismatched nucleotide is shown above the rest of the sequence between its neighbors.

This classification is based in part on sequence homology among these ligands, but in greater part on the basis of a shared secondary structure motif: a three-way helix junction with a three nucleotide loop at the branch point (FIG. 1) (SEQ ID NO:82). These ligands were subdivided into two groups; for ligands in group A, the loop at the branch point has an invariant sequence AGC and in group B, that sequence is G(T/G)(C/T). The proposed consensus secondary structure motif is supported by base-pairing covariation at non-conserved nucleotides in the helices (Table 4). Since the three-way junctions are encoded in continuous DNA strands, two of the helices end in loops at the distal end from the junction. These loops are highly variable, both in length and in sequence. Furthermore, through circular permutation of the consensus motif, the loops occur in all three helices, although they are most frequent in helices II and III. Together these observations suggest that the regions distal from the helix junction are not important for high affinity binding to PDGF-AB. The highly conserved nucleotides are indeed found near the helix junction (Table 3, FIG. 1).

The minimal sequence necessary for high affinity binding was determined for six best ligands to PDGF-AB. In general, the information about the 3' and 5' minimal sequence boundaries can be obtained by partially fragmenting the nucleic acid ligand and then selecting for the fragments that retain high affinity for the target. With RNA ligands, the fragments can be conveniently generated by mild alkaline hydrolysis (Tuerk et al., (1990) *J. Mol. Biol.* 213: 749–761; Jellinek et al., (1994) Biochemistry 33: 10450–10456; Jellinek et al., (1995) *Biochemistry.* 34: 11363–11372; Green et al., (1995) *J. Mol. Biol.* 247: 60–68). Since DNA is more resistant to base, an alternative method of generating fragments is needed for DNA. To determine the 3' boundary, a population of ligand fragments serially truncated at the 3' end was generated by extending the 5' end-labeled primer annealed to the 3' invariant sequence of a DNA ligand using the dideoxy sequencing method. This population was affinity-selected by nitrocellulose filtration and the shortest fragments (truncated from the 3' end) that retain high affinity binding for PDGF-AB were identified by polyacrylamide gel electrophoresis. The 5' boundary was determined in an analogous manner except that a population of 3' end-labeled ligand fragments serially truncated at the 5' end was generated by limited digestion with lambda exonuclease. The minimal ligand is then defined as the sequence between the two boundaries. It is important to keep in mind that, while the information derived from these experiments is useful, the suggested boundaries are by no means absolute since the boundaries are examined one terminus at the time. The untruncated (radiolabeled) termini can augment, reduce or have no effect on binding (Jellinek et al., (1994) *Biochemistry* 33: 10450–10456).

Figure 2:
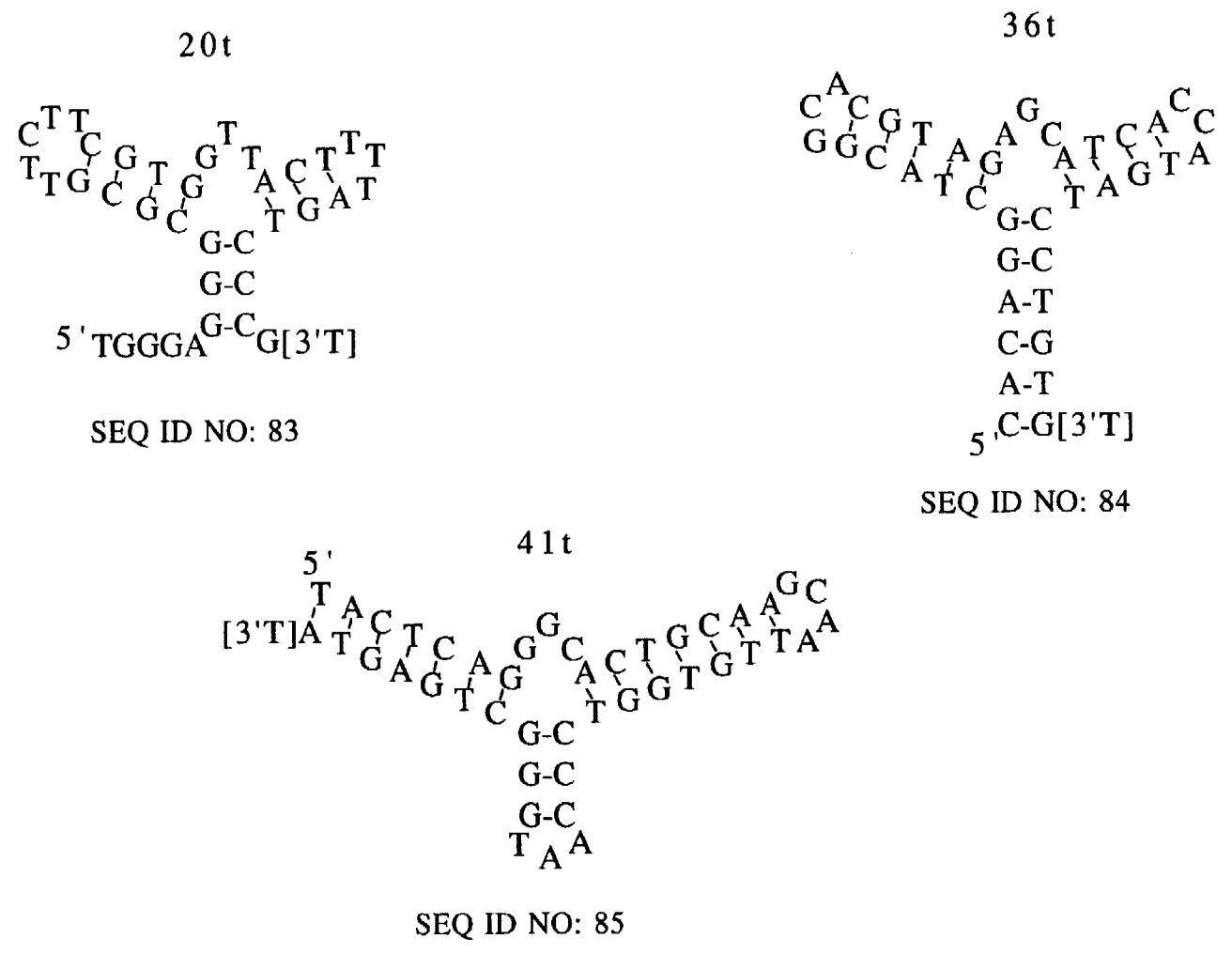

Of the six minimal ligands for which the boundaries were determined experimentally, two (20t(SEQ ID NO:83) and 41t;(SEQ ID NO:85) truncated versions of ligands 20 and 41) bound with affinities comparable (within a factor of 2) to their full-length analogs and four had considerably lower affinities. The two minimal ligands that retained high affinity binding to PDGF, 20t and 41t, contain the predicted three-way helix junction secondary structure motif (FIG. 2) (SEQ ID NOS:83–85). The sequence of the third minimal ligand that binds to PDGF-AB with high affinity, 36t, was deduced from the knowledge of the consensus motif (FIG. 2). In subsequent experiments, we found that the single-stranded region at the 5' end of ligand 20t is not important for high affinity binding. Furthermore, the trinucleotide loops on helices II and III in ligand 36t (GCA and CCA) can be replaced with pentaethylene glycol spacers (infra). These experiments provide further support for the importance of the helix junction region in high affinity binding to PDGF-AB.

Figure 3A:
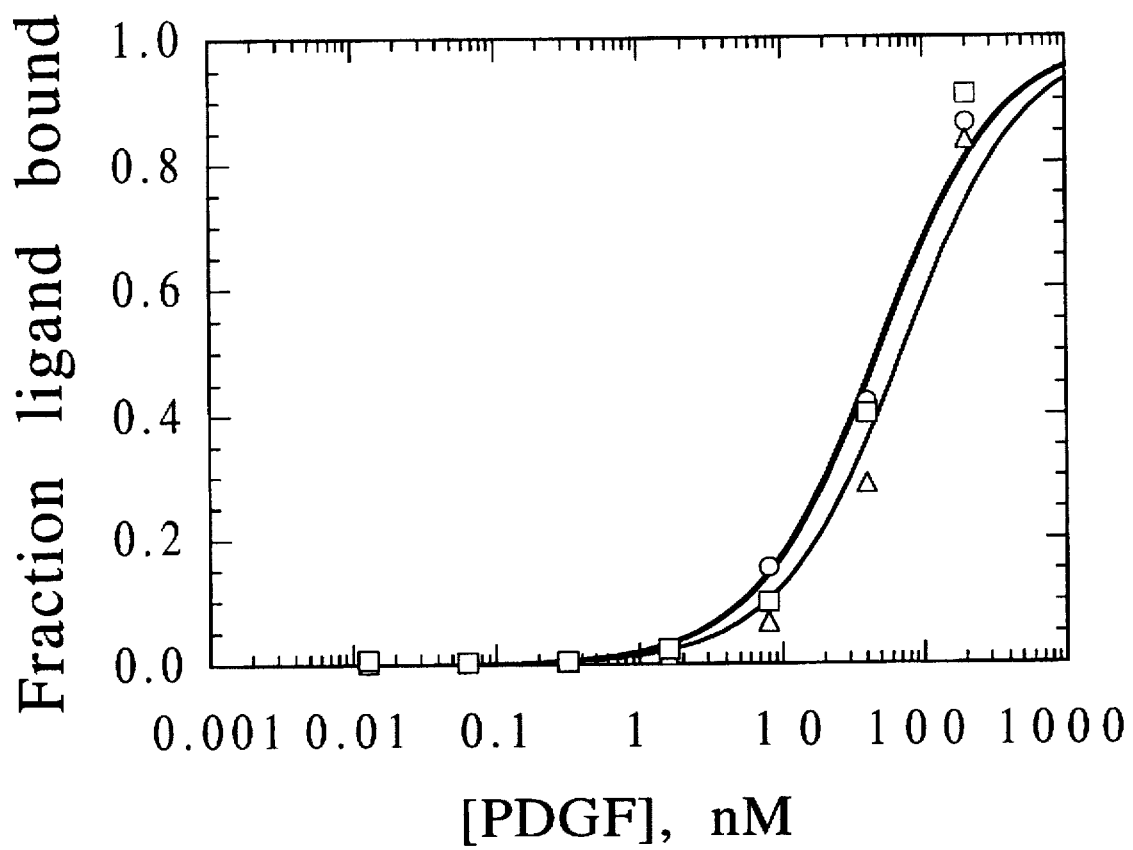
FIGS. 3A–3C show the binding of minimal high affinity DNA ligands to PDGF. The fraction of $^{32}$P 5' end-labeled DNA ligands bound to varying concentrations of PDGF was determined by the nitrocellulose filter binding method. Minimal ligands tested were 20t (o), 36t (Δ), and 41t (■). Oligonucleotide concentrations in these experiments were ≈10 pM (PDGF-AB and PDGF-BB) and ≈50 pM (PDGF AA). Data points were fitted to eq. 1 (for binding of the DNA ligands to PDGF-AA) or to eq. 2 (for binding to PDGF AB and BB) using the non-linear least squares method. Binding reactions were done at 37° C. in binding buffer (PBSM with 0.01% HSA).
Figure 3B:
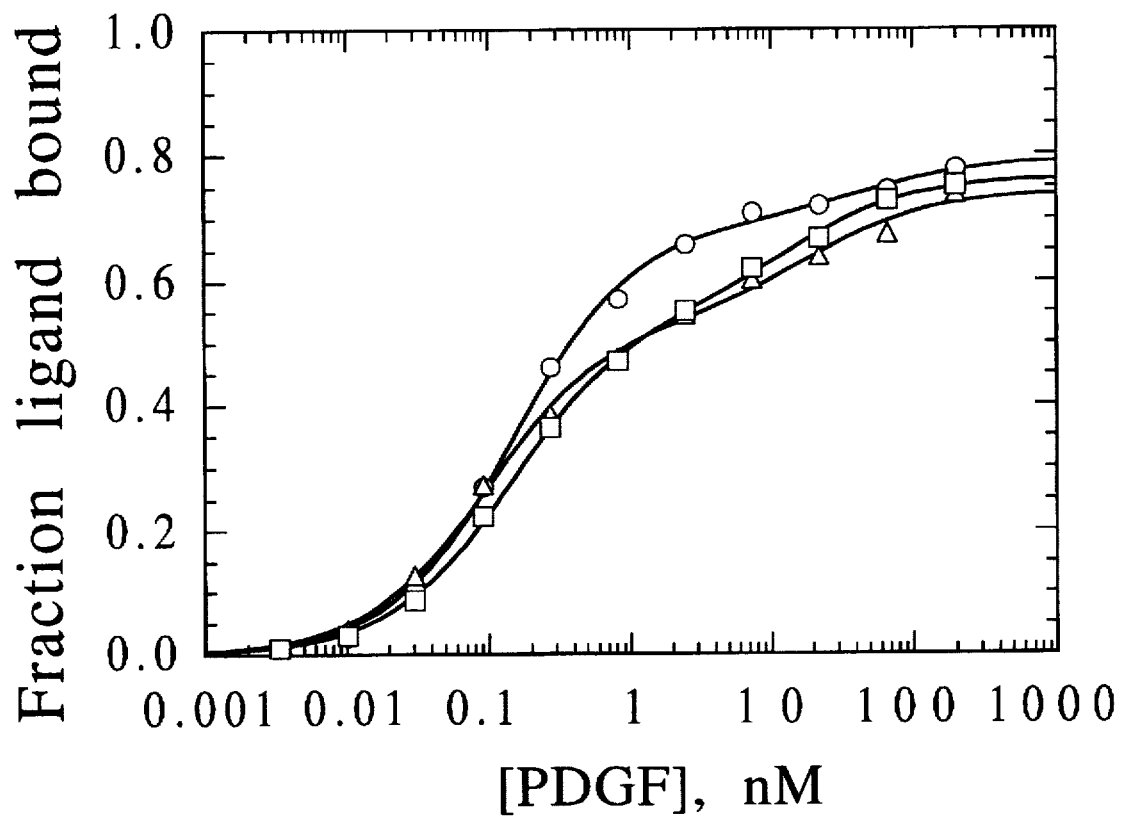
Figure 3C:
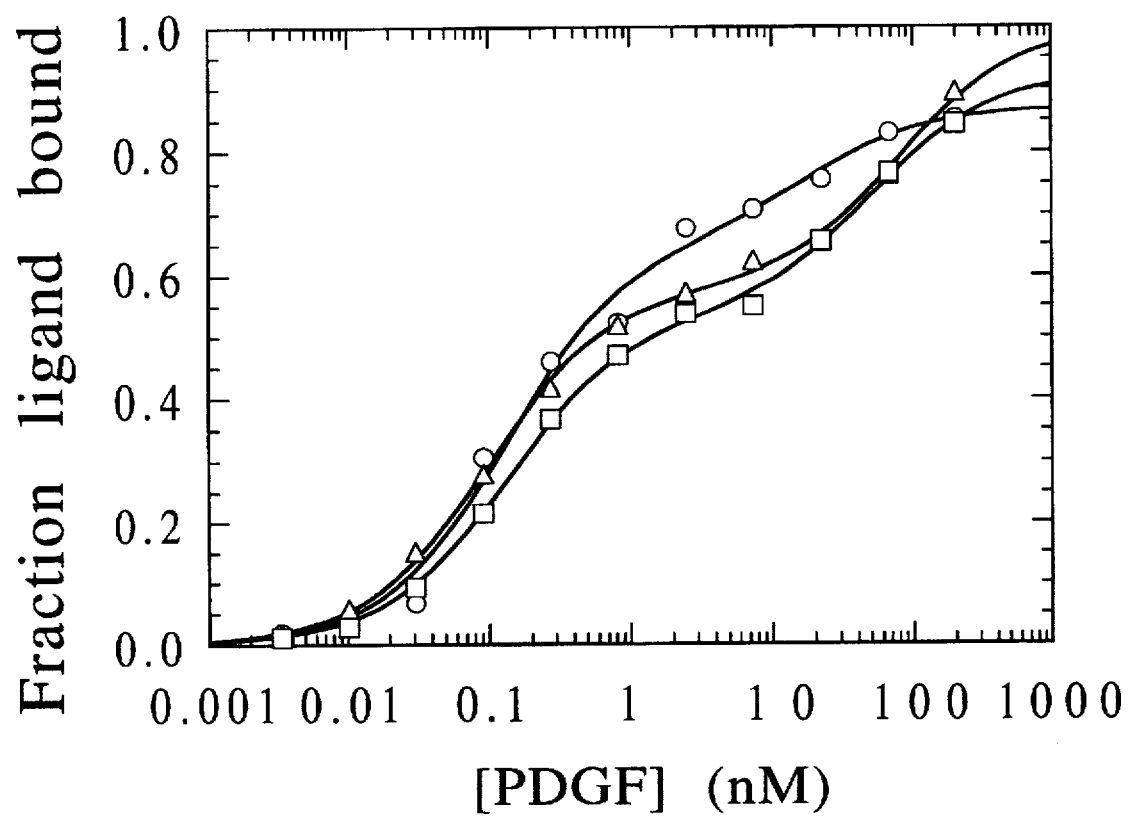

The binding of minimal ligands 20t, 36t, and 41t to varying concentrations of PDGF-AA, PDGF-AB and PDGF-BB is shown in FIG. 3. In agreement with the binding properties of their full length analogs, the minimal ligands bind to PDGF-AB and PDGF-BB with substantially higher affinity than to PDGF AA (FIG. 3, Table 4). In fact, their affinity for PDGF-AA is comparable to that of random DNA (data not shown). The binding to PDGF-AA is adequately described with a monophasic binding equation while the binding to PDGF-AB and PDGF-BB is notably biphasic. In previous SELEX experiments, biphasic binding has been found to be a consequence of the existence of separable nucleic acid species that bind to their target protein with different affinities (Jellinek et al., (1995) *Biochemistry* 34: 11363–11372) and unpublished results). The identity of the high and the low affinity fractions is at present not known. Since these DNA ligands described here were synthesized chemically, it is possible that the fraction that binds to PDGF-AB and PDGF-BB with lower affinity represents chemically imperfect DNA. Alternatively, the high and the low affinity species may represent stable conformational isomers that bind to the PDGF B-chain with different affinities. In any event, the higher affinity binding component is the most populated ligand species in all cases (FIG. 3). For comparison, a 39-mer DNA ligand that binds to human thrombin with a $K_d$ of 0.5 nM (ligand T39 (SEQ ID NO.:88): 5'-CAGTCCGTGGTAGGGCAGGTTGGGGTG ACTTCGTGGAA[3'T], where [3'T] represents a 3'-3' linked thymidine nucleotide added to reduce 3'-exonuclease degradation) and has a predicted stem-loop structure, binds to PDGF-AB with a $K_d$ of 0.23 μM (data not shown).

Figure 4:
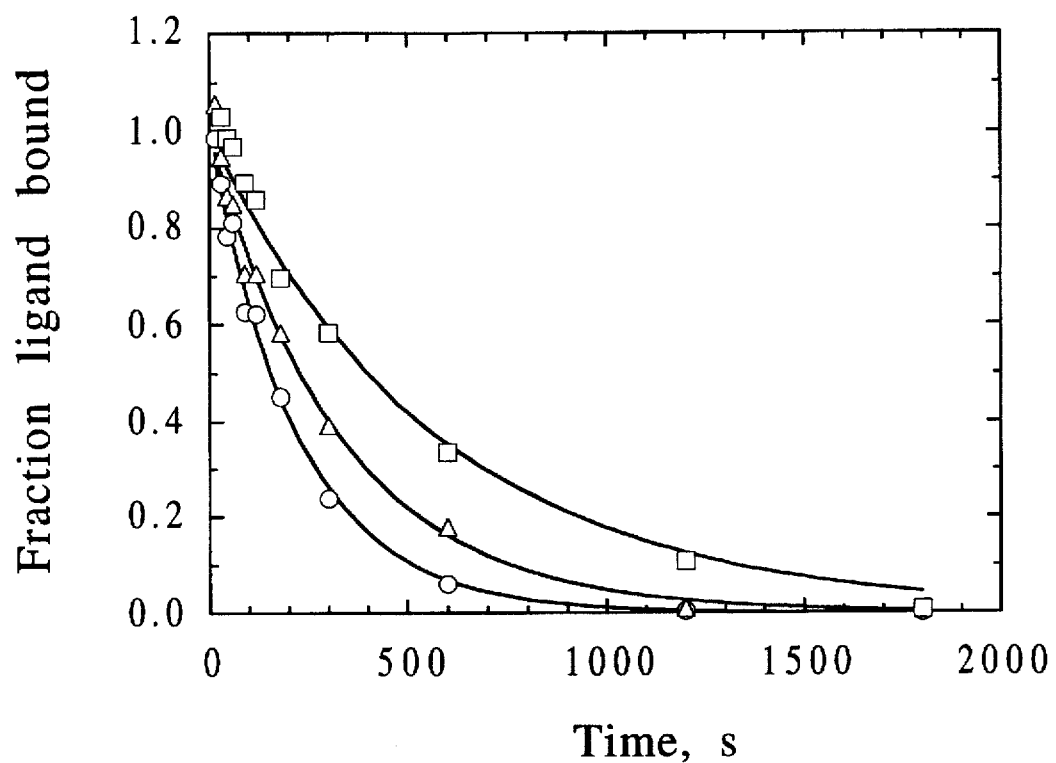
FIG. 4 shows the dissociation rate determination for the high affinity interaction between the minimal DNA ligands and PDGF AB. The fraction of 5' $^{32}$P end-labeled ligands 20t (o), 36t (Δ), and 41t (■), all at 0.17 nM, bound to PDGF AB (1 nM) was measured by nitrocellulose filter binding at the indicated time points following the addition of a 500-fold excess of the unlabeled competitor. The dissociation rate constant ($k_{off}$) values were determined by fitting the data points to eq 3. The experiments were performed at 37° C. in binding buffer.

To evaluate the kinetic stability of the PDGF-AB/DNA complexes, we determined the dissociation rates at 37° C. for the complexes of minimal ligands 20t, 36t and 41t with PDGF-AB by measuring the amount of radiolabeled ligands (0.17 nM) bound to PDGF-AB (1 nM) as a function of time following the addition of a large excess of unlabeled ligands (FIG. 4). At these protein and DNA ligand concentrations, only the high affinity fraction of the DNA ligands binds to PDGF-AB. The following values for the dissociation rate constants were obtained by fitting the data points shown in FIG. 4 to the first-order rate equation: $4.5 \pm 0.2 \times 10^{-3}$ s$^{-1}$ ($t_{1/2}$=2.6 min) for ligand 20t, $3.0 \pm 0.2 \times 10^{-3}$ s$^{-1}$ ($t_{1/2}$=3.8 min) for ligand 36t, and $1.7 \pm 0.1 \times 10^{-3}$ s$^{-1}$ ($t_{1/2}$=6.7 min) for ligand 41t. The association rates calculated for the dissociation constants and dissociation rate constants ($k_{on}=k_{off}/K_d$) are $3.1 \times 10^7$ M$^{-1}$ s$^{-1}$ for 20t, $3.1 \times 10^7$ M$^{-1}$ s$^{-1}$ for 36t and $1.2 \times 10^7$ M$^{-1}$ s$^{-1}$ for 41t.

Figure 5:
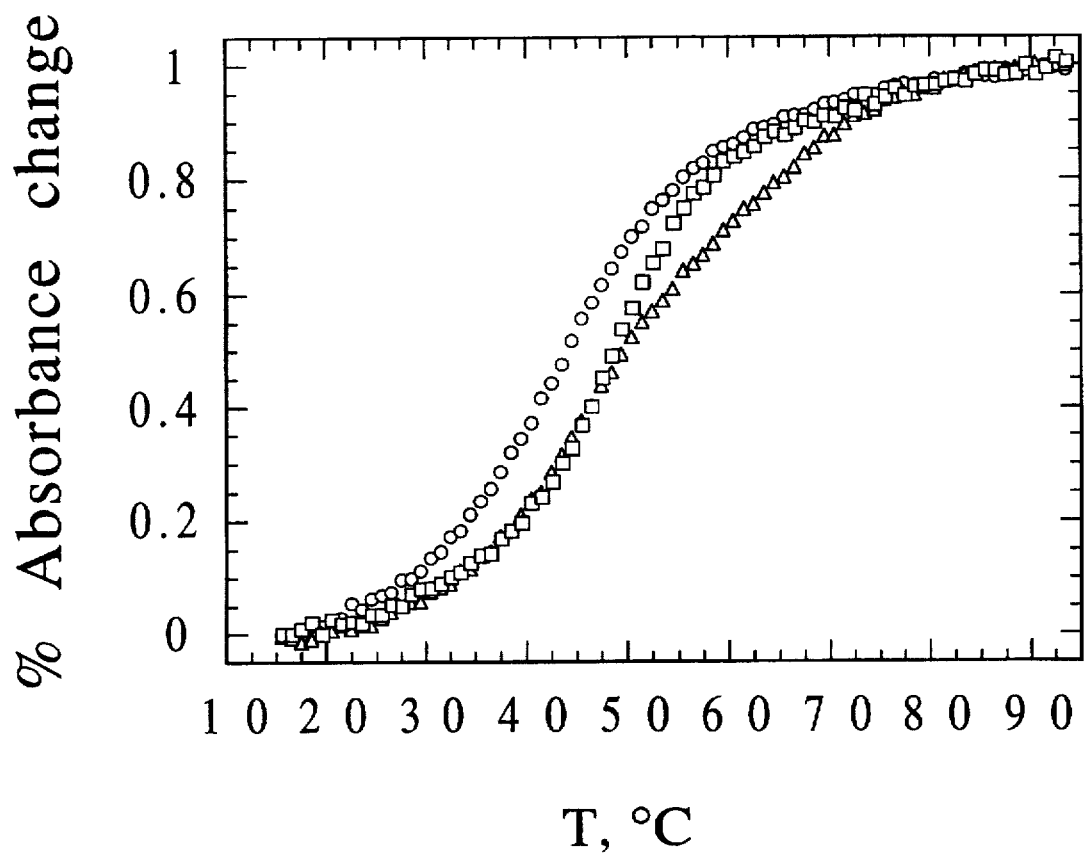
FIG. 5 shows the thermal denaturation profiles for the minimal high affinity DNA ligands to PDGF-AB. The change in absorbance at 260 nm was measured in PBS containing 1 mM $MgCl_2$ as a function of temperature for ligands 20t (o), 36t (Δ), and 41t (■).

Melting temperatures ($T_m$'s) were determined for minimal ligands 20t, 36 t and 41t from the UV absorption vs. temperature profiles (FIG. 5). At the oligonucleotide concentrations used in these experiments (320–440 nM), only the monomeric species were observed as single bands on non-denaturing polyacrylamide gels. The $T_m$ values were obtained from the first derivative replots of the melting profiles. Ligands 20t and 41t exhibited monophasic melting with $T_m$ values of 44° C. and 49° C. The melting profile of ligand 36t was biphasic, with the Tm value of 44° C. for the first (major) transition and ≈63° C. for the second transition.

To determine the sites on the DNA ligands and PDGF that are in close contact, we performed a series of photo-crosslinking experiments with 5'-iodo-2'-deoxyuridine (IdU)-substituted DNA ligands 20t, 36t and 41t. Upon monochromatic excitation at 308 nm, 5-iodo- and 5-bromo-substituted pyrimidine nucleotides populate a reactive triplet state following intersystem crossing from the initial n to π* transition. The excited triplet state species then reacts with electron rich amino acid residues (such as Trp, Tyr and His) that are in its close proximity to yield a covalent crosslink. This method has been used extensively in studies of nucleic acid-protein interactions since it allows irradiation with >300 nm light which minimizes photodamage (Willis et al., (1994) *Nucleic Acids Res.* 22: 4947–4952; Stump, W. T., and Hall, K. B. (1995) *RNA* 1: 55–63; Willis et al., (1993) *Science* 262: 1255–1257; Jensen et al., (1995) *Proc. Natl. Acad. Sci., U.S.A.* 92: 12220–12224). We synthesized analogs of ligands 20t, 36t and 41t in which all thymidine residues were replaced with IdU residues using the solid phase phosphoramidite method. The affinity of these IdU-substituted ligands for PDGF-AB was somewhat enhanced compared to the unsubstituted ligands and based on the appearance of bands with slower electrophoretic mobility on 8% polyacrilamide/7M urea gels, all three 5' end-labeled IdU-substituted ligands crosslinked to PDGF-AB upon irradiation at 308 nm (data not shown). The highest crosslinking efficiency was observed with IdU-substituted ligand 20t. To identify the specific IdU position(s) responsible for the observed crosslinking, we tested seven singly or multiply IdU-substituted analogs of 20t for their ability to photo-crosslink to PDGF-AB: ligands 20t-I1 through 20t-I7 (5'-TGGGAGGGCGCGT$^1$T$^1$CT$^1$T$^1$CGT$^2$GGT$^3$T$^4$ACT$^5$T$^6$T$^6$ T$^6$AGT$^7$CCCG-3' (SEQ ID NO:89–95) where the numbers indicate IdU substitutions at indicated thymidine nucleotides for the seven ligands). Of these seven ligands, efficient crosslinking to PDGF-AB was observed only with ligand 20t-I4 SEQ ID NO:96. The photo-reactive IdU position corresponds to the 3' proximal thymidine in the loop at the helix junction (FIG. 2).

To identify the crosslinked amino acid residue(s) on PDGF-AB, a mixture of 5' end-labeled 20t-I4 and PDGF-AB was incubated for 15 min at 37° C. followed by irradiation at 308 nm. The reaction mixture was then digested with modified trypsin and the crosslinked fragments resolved on an 8% polyacrylamide/7M urea gel. Edman degradation of the peptide fragment recovered from the band that migrated closest to the free DNA band revealed the amino acid sequence KKPIXKK (SEQ ID NO:96), where X indicates a modified amino acid that could not be identified with the 20 derivatized amino acid standards. This peptide sequence, where X is phenylalanine, corresponds to amino acids 80–86 in the PDGF-B chain (Johnsson et al., (1984) *EMBO J.* 3: 921–928) which in the crystal structure of PDGF-BB comprises a part of solvent-exposed loop III (Oefner et al., (1992) *EMBO J.* 11: 3921–3926). In the PDGF A-chain, this peptide sequence does not occur (Betsholtz et al., (1986) *Nature* 320, 695–699). Together, these data establish a point contact between a specific thymidine residue in ligand 20t and phenylalanine 84 of the PDGF β-chain.

Figure 6:
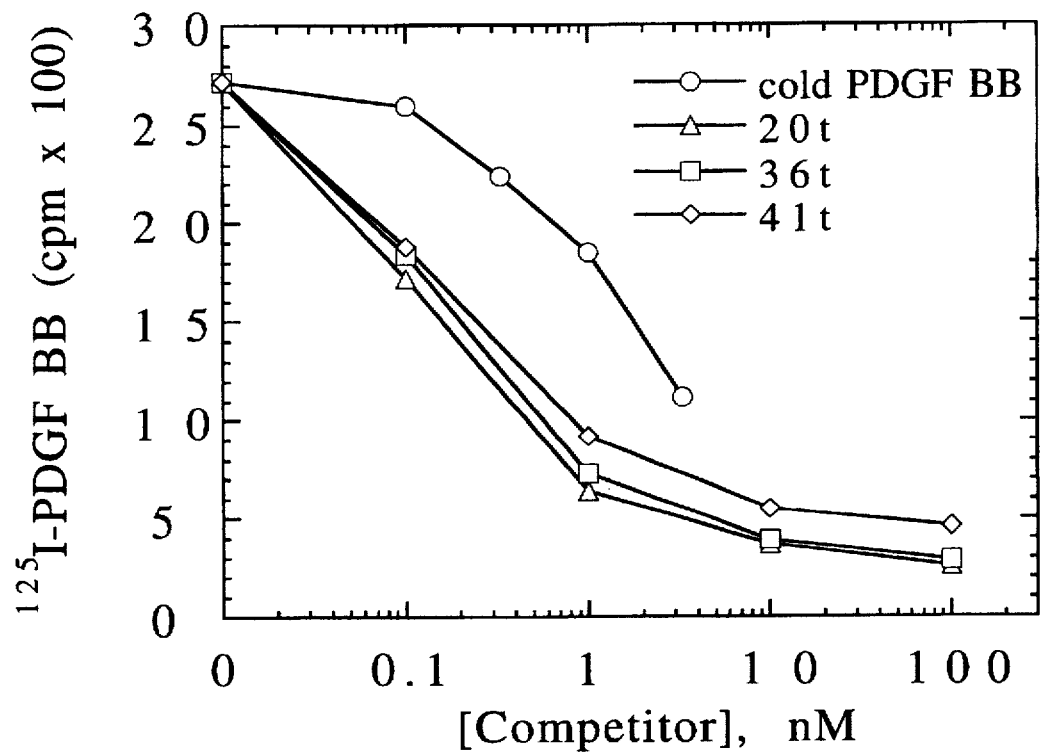
FIG. 6 shows the effect of DNA ligands on the binding of $^{125}$I-PDGF-BB and $^{125}$I-PDGF-AA to PDGF α-receptors expressed in PAE cells.

In order to determine whether the DNA ligands to PDGF were able to inhibit the effects of PDGF isoforms on cultured cells, we first determined their effects on binding of $^{125}$I-labeled PDGf isoforms to PDGF α- and β-receptors stabley expressed in porcine aortic endothelial (PAE) cells by transfection. Ligands 20t, 36t and 41t all efficiently inhibited the binding of $^{125}$I-PDGF-BB to PDGF α-receptors (FIG. 6) or PDGF β-receptors (data not shown), with half maximal effects around 1 nM of DNA ligand. DNA ligand T39, directed against thrombin and included as a control, showed no effect. None of the ligands were able to inhibit the binding of $^{125}$I-PDGF-AA to the PDGF a-receptor (FIG. 6), consistent with the observed specificity of ligands 20t, 36t and 41t for PDGF-BB and PDGF-AB.

Figure 7:
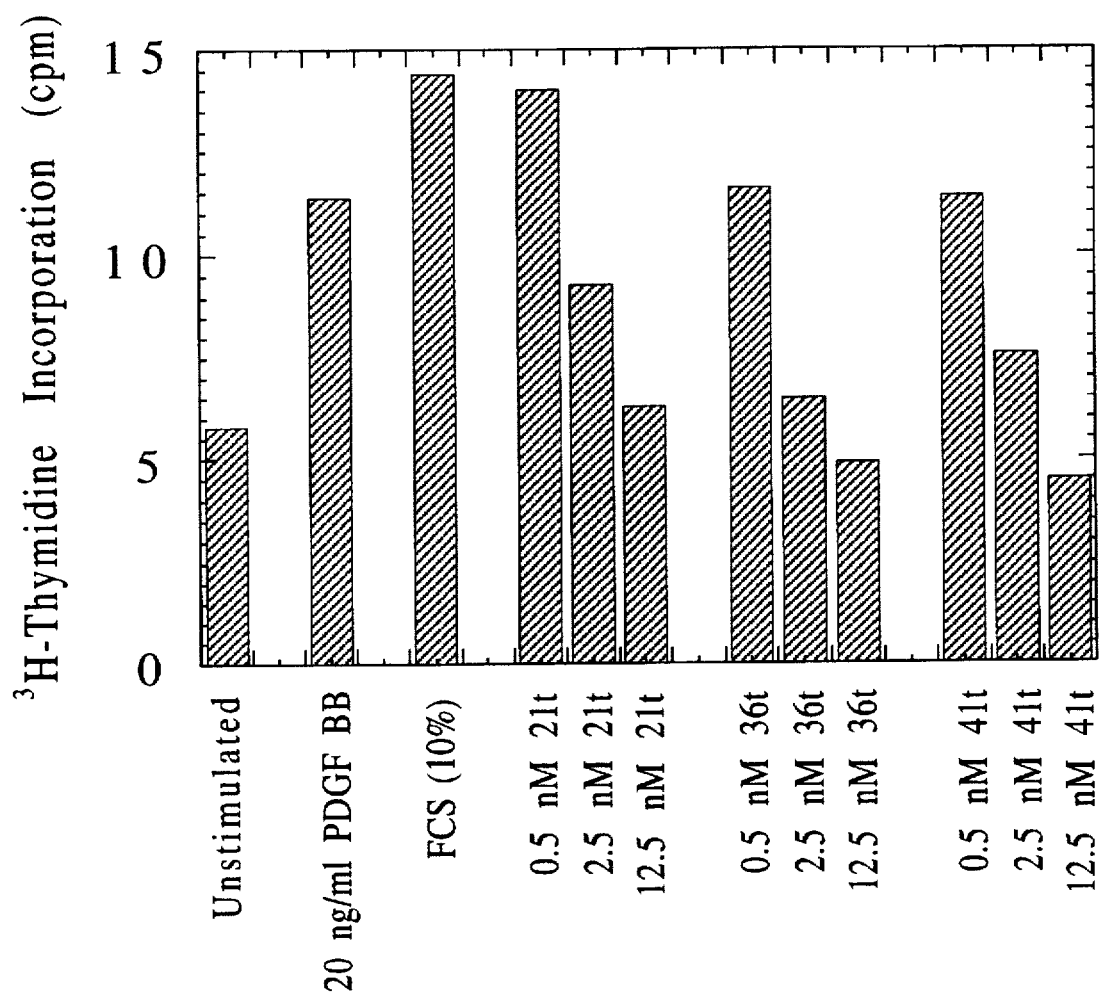
FIG. 7 shows the effect of DNA ligands on the mitogenic efect of PDGF-BB on PAE cells expressing the PDGF β-receptors.

We furthermore investigated the ability of the DNA ligands to inhibit the mitogenic effects of PDGF-BB on PAE cells expressing PDGF β-receptors. As shown in FIG. 7, the stimulatory effect of PDGF-BB on [$^{3}$H]thymidine incorporation was neutralized by ligands 20t, 36t and 41t. Ligand 36t exhibited half maximal inhibition at the concentration of 2.5 nM; ligands 41t was slightly more efficient and 20t slightly less efficient. The control ligand T39 had no effect. Moreover, none of the ligands inhibited the stimulatory effects of fetal calf serum on [$^{3}$H]thymidine incorporation in these cells, showing that the inhibitory effects are specific for PDGF.

Figure 8:
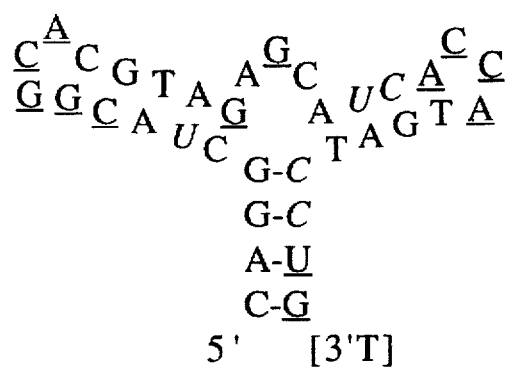
FIG. 8 shows the 2'-O-methyl-2'-deoxy- and 2'-fluoro-2'-deoxyribonucleotide-substitution pattern compatible with high affinity binding to PDGF-AB. Underlined symbols indicate 2'-O-methyl-2'-deoxynucleotides; italicized symbols indicate 2'-fluoro-2'-deoxynucleotides normal font indicates 2'-deoxyribonucleotides; [3'T] indicates inverted orientation (3'3') thymidine nucleotide (Glen Research, Sterling, Va.); PEG in the loops of helices II and III indicates pentaethylene glycol spacer phosphoramidite (Glen Research, Sterling, Va.).
Figure 8:
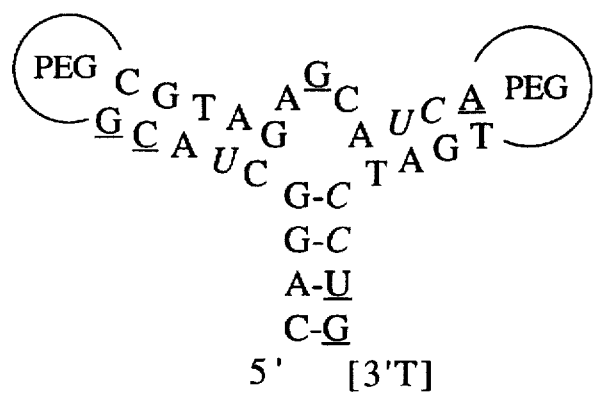

The stability of nucleic acids to nucleases is an important consideration in efforts to develop nucleic acid-based therapeutics. Recent experiments done in our laboratories have shown that many, and in some cases most of the nucleotides in SELEX-derived ligands can be substituted with modified nucleotides that resist nuclease digestion, without compromising high affinity binding (Green et al., (1995) *Chemistry and Biology* 2: 683-695; Green et al., (1995) *J. Mol. Biol.* 247, 60-80. Preliminary experiments of this type with the DNA ligands reported here suggest that substitutions with modified nucleotides are tolerated at many positions (FIG. 8) (SEQ ID NO:86-87). Specifically, we have examined the substitution of 2'-O-methyl-2'-deoxy- and 2'-fluoro-2'-deoxyribonucleotides for 2'-deoxyribonucleotides in ligand 36t, by examining the PDGF-AB binding properties of singly or multiply substituted ligand 36t. The substitution pattern indicated in FIG. 8 is compatible with high affinity binding to PDGF-AB. Furthermore, this ligand tolerates the substitution of pentaethylene glycol spacers (Glen Research, Sterling, Va.) for the trinucleotide loops at the ends of helices II and III (FIG. 8). These DNA ligands therefore represent lead compounds for a novel class of high affinity, specific antagonists of PDGF-AB and PDGF-BB.

EXAMPLE 3

EXPERIMENTAL PROCEDURE FOR EVOLVING 2'-FLUORO-2'-DEOXYPYRIMIDINE RNA LIGANDS TO PDGF AND RNA SEQUENCES OBTAINED.

2'-FLUORO-2'-DEOXYPYRIMIDINE RNA SELEX

SELEX with 2'-fluoro-2'-deoxypyrimidine RNA targeting PDGF AB was done essentially as described previously (vide supra, and Jellinek et al., 1993, 1994: supra) using the primer template set as shown in Table 6. Briefly, the 2'-fluoro-2'-deoxypyrimidine RNA for affinity selections was prepared by in vitro transcription from synthetic DNA templates using T7 RNA polymerase (Milligan et al. *Nucl. Acids Res.*, 15: 8783 (1987)). The conditions for in vitro transcription described in detail previously (Jellinek et al. (1994) supra) were used, except that higher concentration (3 mM) of the 2'-fluoro-2'-deoxypyrimidine nucleoside triphosphates (2'-F-UTP and 2'-F-CTP) was used compared to ATP and GTP (1 mM). Affinity selections were done by incubating PDGF AB with 2'-fluoro-2'-deoxypyrimidine RNA for at least 15 min at 37° C. in PBS containing 0.01% human serum albumin. Partitioning of free RNA from protein-bound RNA was done by nitrocellulose filtration as described (Jellinek et al., 1993, 1994: supra). Reverse transcription of the affinity-selected RNA and amplification by PCR were done as described previously (Jellinek et al. (1994) supra). Nineteen rounds of SELEX were performed, typically selecting between 1-12% of the input RNA. For the first eight rounds of selection, suramin (3-15 μM) was included in the selection buffer to increase the selection pressure. The affinity-enriched pool (round 19) was cloned and sequenced as described (Schneider et al., 1992 supra). Forty-six unique sequences have been identified, and the sequences are shown in Table 7. The unique-sequence ligands were screened for their ability to bind PDGF AB with high affinity. While random 2'-fluoropyrimidine RNA (Table 6) bound to PDGF with a dissociation constant (Kd) of 35±7 nM, many of the affinity-selected ligands bound to PDGF AB with ≈100-fold higher affinities. Among the unique ligands, clones 9 ($K_d$=91±16 pM), 11 ($K_d$=120±21 pM), 16 ($K_d$=116±34 pM), 23 ($K_d$=173±38 pM), 25 ($K_d$=80±22 pM), 37 ($K_d$=97±29 pM), 38 ($K_d$=74±39 pM), and 40 ($K_d$=91±32 pM) exhibited the highest affinity for PDGF AB (binding of all of these ligands to PDGF AB is biphasic and the $K_d$ for the higher affinity binding component is given).

TABLE 1

Starting DNA and PCR primers for the ssDNA SELEX experiment.

| | SEQ ID NO. |
|---|---|
| Starting ssDNA: | |
| 5'-ATCCGCCTGATTAGCGATACT[-40N-]ACTTGAGCAAAATCACCTGCAGGGG-3' | 1 |
| PCR Primer 3N2*: | |
| 5'-BBBCCCCTGCAGGTGATTTTGCTCAAGT-3' | 2 |
| PCR Primer 5N2**: | |
| 5'-CCGAAGCTTAATACGACTCACTATAGGG<u>ATCCGCCTGATTAGCGATACT</u>-3' | 3 |

*B = biotin phosphoramidite (e.g., Glen Research, Sterling, VA)
**For rounds 10, 11, and 12, the truncated PCR primer 5N2 (underlined) was used to amplify the template.

TABLE 2

Unique Sequences of the ssDNA high affinity ligands to PDGF.

5'- ATCCGCCTGATTAGCGATACT [40N] ACTTGAGCAAAATCACCTGCAGGGG-3'

SEQ ID

TABLE 3

| SEQ ID NO: | Group A | | HELIX II | | HELIX I | | HELIX III | |
|---|---|---|---|---|---|---|---|---|
| 8 | | =AGGG | AGGA | TACG | TCTG | AGC | ATCac 3' | |
| 23 | | ACCGGG | CTAC | TTC | GTAG | AGC | ATC | 5'ATGTGAT | CCCTGCAG= |
| | | | | | | | | GAT | CCCGGTGCTCG |
| 26 | | tGGG | CGACC | TTCT | GGACG | AGC | ATCAC | CTAT | GTGAT CCCG |
| 20 | | ctGAGG | CATG | TTAA | CATG | AGC | ATCGT | CTC | ACGAT CCTCAGCC |
| 21 | | CCACAGG | CTACG | GCA | CGTAG | AGC | ATCA | CCA | TGAT CCTGTG |
| 35 | | CCTGCAGG | TCC | CCT | GGA | AGC | ATC | TCC | GAT CCCAGactt |
| 38 | AAAGTCGTG | CAGG | CGAAC | GTA | GGTCG | AGG | ATCC | ATT | GGAT CCCTTC |
| 44 | | AAAGGG | CTGC | | GCAG | AGC | ATCac 3' | | |
| 22 | | GCGGG | CATG | GCA | CATG | AGC | ATC | TCT | GAT CCCGGCAATCCTC |
| 7 | | =AGG | CAGGATAAC | | GTCCTG | AGC | ATC | | 5'AGGTGAT CCCTGCAA= |
| 9 | | =GGG | CTGC | GCAAAATA | GCAG | AGC | ATCac 3' | | 5'CACGTGAT CCCATAA= |
| SEQ ID NO: | Group B | | | | | | | |
| 19 | | GCTCGTAGG | GGGCGA | TTCTT | TCGCC | GTT | ACT | TCC | AGT CCTac |
| 4 | | tactAGG | CTT | GACA | AAG | GGC | ACCAT | GGTTAGTGGT | CCTAGTa |
| | | | C | | | | | | |
| 34 | | ctCAAGTAGGG | CGGAC | ACAC | GTCCG | GGC | ACC | TAA | GGT CCCAacttgag |
| 15 | | | CGCCCTAAACAA | AGGGTG | GTC | ACT | TCT | AGT | CCCAGGA |
| 18 | | ctGGG | CGCG | TTCTT | CGTG | GTT | ACT | TTT | AGT CCCCG |
| 17 | | ATGGGAGGG | CGTG | AATGTC | CACG | GGT | ACC | TCC | GGT CCCAAAGAG |
| 31 | | ctTTGGG | CTCGg | GAT | TCGTG | GTC | ACC | TTC | AGT CCCGGATATA |
| 16 | | TCCGGG | | | | | ATC | | AGT CCCact |
| 32 | | =AGGG | CAG | CCCTAA | CTG | GTC | acttgagc3' | | 5'TCCGCGCAAGT CCCTGGTAA= |
| 18 | | ACGGGAGGG | CACG | TTCTT | CGTG | GTT | ACT | TTT | ACT CCCG |
| 35 | | | CTGAGTa 3' | 5'tactCAG | GGC | ACTGCAAGCAATTGTGGT | CCCAAT= | | |
| 41 | | | | | | | | | |
| 14 | | GTGGGTGGGATCGGGG | ATG | | CCTC | GTC | ACT | ICT | AGT CCCact |

TABLE 4

Frequency of base pairs in the helical regions of the consensus motif shown in FIG. 1.

| Position[a] | Base pair[b] | | | | | | |
|---|---|---|---|---|---|---|---|
| | AT | TA | GC | CG | TG | GT | other |
| I-1 | 0 | 0 | 21 | 0 | 0 | 0 | 0 |
| I-2 | 0 | 0 | 21 | 0 | 0 | 0 | 0 |
| I-3 | 5 | 0 | 16 | 0 | 0 | 0 | 0 |
| I-4 | 3 | 5 | 1 | 4 | 1 | 0 | 7 |
| I-5 | 2 | 3 | 3 | 4 | 0 | 0 | 9 |
| II-1 | 0 | 1 | 2 | 17 | 0 | 0 | 1 |
| II-2 | 5 | 5 | 5 | 1 | 0 | 4 | 1 |
| II-3 | 3 | 4 | 7 | 6 | 0 | 0 | 1 |
| II-4 | 3 | 0 | 8 | 5 | 0 | 0 | 4 |
| III-1 | 21 | 0 | 0 | 0 | 0 | 0 | 0 |
| III-2 | 0 | 10 | 0 | 11 | 0 | 0 | 0 |
| III-3 | 0 | 7 | 0 | 13 | 1 | 0 | 0 |

[a]Helices are numbered with roman numerals as shown in FIG. 1. Individual base pairs are numbered with arabic numerals starting with position 1 at the helix junction and increasing with increased distance from the junction.

[b]We have included the TG and GT base pairs to the Watson-Crick base pairs for this analysis. There is a total of 21 sequences in the set.

TABLE 5

Affinities of the minimal DNA ligands to PDGF AA, PDGF AB and PDGF BB.

| | $K_d$, nM | | |
|---|---|---|---|
| Ligand | PDGF AA[a] | PDGF AB[b] | PDGF BB[b] |
| 20t | 47 ± 4 | 0.147 ± 0.011 | 0.127 ± 0.031 |
| 36t | 72 ± 12 | 0.094 ± 0.011 | 0.093 ± 0.009 |
| 41t | 49 ± 8 | 0.138 ± 0.009 | 0.129 ± 0.011 |

[a]Data points shown in the upper panel of FIG. 3 were fitted to eq 1 (Example 1).

[b]Data points in the middle and lower panels of FIG. 3 were fitted to eq. 2. The dissociation constant ($K_d$) values shown are for the higher affinity binding component. The mole fraction of DNA that binds to PDGF AB or PDGF BB as the high affinity component ranges between 0.58 to 0.88. The $K_d$ values for the lower affinity interaction range between 13 to 78 nM.

TABLE 6

Starting RNA and PCR primers for the 2'-fluoropyrimidine RNA SELEX experiment.

| Starting 2'-fluoropyrimidine RNA: | SEQ ID NO |
|---|---|
| Starting RNA: 5'-GGGAGACAAGAAUAACGCUCAA[-50 N-]UUCGACAGGAGGCUCACAACAGGC-3' | 36 |
| PCR Primer 1: 5'-TAATACGACTCACTATAGGGAGACAAGAATAACGCTCAA-3' | 37 |
| PCR Primer 2: 5'-GCCTGTTGTGAGCCTCCTGTCGAA-3' | 38 |

TABLE 7

Sequences of the 2'-fluoropyrimidine RNA high affinity ligands to PDGF AB.

| | SEQ ID NO. |
|---|---|
| 1 CGGUGGCAUUUCUUCACUUCCUUCUCGCUUUCUCGCGUUGGGCNCGA | 39 |
| 2 CCAACCUUCUGUCGGCGUUGCUUUUUGGACGGCACUCAGGCUCCA | 40 |
| 3 UCGAUCGGUUGUGUGCCGGACAGCCUUAACCAGGGCUGGGACCGAGGCC | 41 |
| 4 CUGAGUAGGGGAGGAAGUUGAAUCAGUUGUGGCGCCUCUCAUUCGC | 42 |
| 5 CAGCACUUUCGCUUUUCAUCAUUUUUUCUUUCCACUGUUGGGCGCGGAA | 43 |
| 6 UCAGUGCUGGCGUCAUGUCUCGAUGGGGAUUUUUCUUCAGCACUUUGCCA | 44 |
| 7 UCUACUUUCCAUUUCUCUUUUCUUCUCACGAGCGGGUUUCCAGUGAACCA | 45 |
| 8 CGAUAGUGACUACGAUGACGAAGGCCGCGGGUUGGAUGCCCGCAUUGA | 46 |
| 10 GUCGAUACUGGCGACUUGCUCCAUUGGCCGAUUAACGAUUCGGUCAG | 47 |
| 13 GUGCAAACUUAACCCGGGAACCGCGCGUUUCGAUCGACUUUCCUUUCCA | 48 |
| 15 AUUCCGCGUUCCGAUUAAUCCUGUGCUCGGAAAUCGGUAGCCAUAGUGCA | 49 |
| 16 CGAACGAGGAGGGAGUGGCAAGGGAUGGUUGGAUAGGCUCUACGCUCA | 50 |
| 17 GCGAAACUGGCGACUUGCUCCAUUGGCCGAUAUAACGAUUCGGUUCAU | 51 |
| 18 CGAACGAGGAGGGAGUCGCAAGGGAUGGUUGGAUAGGCUCUACGCUCAA | 52 |
| 19 CGAGAAGUGACUACGAUGACGAAGGCCGCGGGUUGAAUCCCUCAUUGA | 53 |
| 20 AAGCAACGAGACCUGACGCCUGAUGUGACUGUGCUUGCACCCGAUUCUG | 54 |
| 21 GUGAUUCUCAUUCUCAAUGCUUUCUCACAACUUUUUCCACUUCAGCGUGA | 55 |

TABLE 7-continued

Sequences of the 2'-fluoropyrimidine RNA high affinity ligands to PDGF AB.

| | | SEQ ID NO. |
|---|---|---|
| 22 | AAGCAACGAGACUCGACGCCUGAUGUGACUGUGCUUGCACCCGAUUCU | 56 |
| 23 | UCGAUCGGUUGUGUGCCGGACAGCUUUGACCAUGAGCUGGGACCGAGGCC | 57 |
| 24 | NGACGNGUGGACCUGACUAAUCGACUGAUCAAAGAUCCCGCCCAGAUGGG | 58 |
| 26 | CACUGCGACUUGCAGAAGCCUUGUGUGGCGGUACCCCCUUUGGCCUCG | 59 |
| 27 | GGUGGCAUUUCUUCAUUUUCCUUCUCGCUUUCUCCGCCGUUGGGCGCG | 60 |
| 29 | CCUGAGUAGGGGGGAAAGUUGAAUCAGUUGUGGCGCUCUACUCAUUCGCC | 61 |
| 30 | GUCGAAACUGGCGACUUGCUCCAUUGGCCGAUAUAACGAUUCGGUUCA | 62 |
| 31 | GCGAUACUGGCGACUUGCUCCAUUGGCCGAUAUAACGAUUCGGCUCAG | 63 |
| 32 | ACGUGGGGCACAGGACCGAGAGUCCCUCCGGCAAUAGCCGCUACCCCACC | 64 |
| 33 | CACAGCCUNANAGGGGGGAAGUUGAAUCAGUUGUGGCGCUCUACUCAUUCGC | 65 |
| 34 | ANGGGNUAUGGUGACUUGCUCCAUUGGCCGAUAUAACGAUUCGGUCAG | 66 |
| 35 | CCUGCGUAGGGNGGGAAGUUGAAUCAGUUGUGGCGCUCUACUCAUUCGCC | 67 |
| 39 | CGAACGAGGAGGGAGUGGCAAGGGAUGGUUGGAUAGGCUCUACGCUCA | 68 |
| 41 | GUGCAAACUUAACCCGGGAACCGCGCGUUUCGAUUCGCUUUCCNUAUUCCA | 69 |
| 42 | CGAACGAGGAGGGAGUGGCAAGGGACGGUNNAUAGGCUCUACGCUCA | 70 |
| 43 | UCGGUGUGGCUCAGAAACUGACACGCGUGAGCUUCGCACACAUCUGC | 71 |
| 44 | UAUCGCUUUUCAUCAAUUCCACUUUUUCACUCUNAACUUGGGCGUGCA | 72 |
| 45 | GUGCAAACUUAACCCGGGAACCGCGCGUUUCGAUCCUGCAUCCUUUUUCC | 73 |
| 46 | UCGNUCGGUUGUGUGCCGGCAGCUUUGUCCAGCGUUGGGCCGAGGCC | 74 |
| 47 | AGUACCCAUCUCAUCUUUUCCUUUCCUUUCUUCAAGGCACAUUGAGGGU | 75 |
| 49 | CCUGAGUAGGGGGGGAAGUUGAACCAGUUGUGGCNGCCUACUCAUUCNCCA | 76 |
| 51 | CCNNCCUNCUGUCGGCGCUUGUCUUUUUGGACGGGCAACCCAGGGCUC | 77 |
| 52 | CCAACCUNCUGUCGGCGCUUGUCUUUUUGGACGAGCAACUCAAGGCUCGU | 78 |
| 53 | CCAGCGCAGAUCCCGGGCUGAAGUGACUGCCGGCAACGGCCGCUCCA | 79 |
| 54 | UUCCCGUAACAACUUUUCAUUUUCACUUUUCAUCCAACCAGUGAGCAGCA | 80 |
| 55 | UAUCGCUUUCAUCAAAUUCCACUCCUUCACUUCUUUAACUUGGGCGUGCA | 81 |

We claim:

1. A purified and isolated non-naturally occurring DNA ligand to Platelet Derived Growth Factor (PDGF) wherein said ligand is selected from the group consisting of SEQ ID NOS:82–87.

2. A purified and isolated non-naturally occurring nucleic acid ligand to PDGF comprising the conserved structure shown in FIG. 1.

3. The purified and isolated non-naturally occurring DNA ligand to PDGF of claim 1 consisting of the nucleotide sequence of SEQ ID NO:87.

* * * * *

SEQUENCE LISTING ( 1 ) GENERAL INFORMATION:

( i i i ) NUMBER OF SEQUENCES: 96

( 2 ) INFORMATION FOR SEQ ID NO: 1:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 1:

```
ATCCGCCTGA TTAGCGATAC TNNNNNNNNN NNNNNNNNN NNNNNNNNN         50

NNNNNNNNNN NACTTGAGCA AAATCACCTG CAGGGG                      86
```

( 2 ) INFORMATION FOR SEQ ID NO: 2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: N at positions 1-3 is biotin ( x i ) SEQUENCE DESCRIPTION: SEQ ID NO: 2:

```
NNNCCCCTGC AGGTGATTTT GCTCAAGT                               28
```

( 2 ) INFORMATION FOR SEQ ID NO: 3:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 3:

```
CCGAAGCTTA ATACGACTCA CTATAGGGAT CCGCCTGATT AGCGATACT           49
```

( 2 ) INFORMATION FOR SEQ ID NO: 4:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 4:

```
ATCCGCCTGA TTAGCGATAC TAGGCTTGAC AAAGGGCACC ATGGCTTAGT           50

GGTCCTAGTA CTTGAGCAAA TCACCTGCA GGGG                             84
```

( 2 ) INFORMATION FOR SEQ ID NO: 5:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 5:

```
ATCCGCCTGA TTAGCGATAC TCAGGGCACT GCAAGCAATT GTGGTCCCAA           50

TGGGCTGAGT ACTTGAGCAA AATCACCTGC AGGGG                           85
```

( 2 ) INFORMATION FOR SEQ ID NO: 6:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 6:

```
ATCCGCCTGA TTAGCGATAC TCCAGGCAGT CATGGTCATT GTTTACAGTC           50

GTGGAGTAGG TACTTGAGCA AAATCACCTG CAGGGG                          86
```

( 2 ) INFORMATION FOR SEQ ID NO: 7:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 7:

```
ATCCGCCTGA TTAGCGATAC TAGGTGATCC CTGCAAAGGC AGGATAACGT           50
```

CCTGAGCATC ACTTGAGCAA AATCACCTGC AGGGG   85

( 2 ) INFORMATION FOR SEQ ID NO: 8:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 8:

ATCCGCCTGA TTAGCGATAC TATGTGATCC CTGCAGAGGG AGGANACGTC   50

TGAGCATCAC TTGAGCAAAA TCACCTGCAG GGG   83

( 2 ) INFORMATION FOR SEQ ID NO: 9:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 9:

ATCCGCCTGA TTAGCGATAC TCACGTGATC CCATAAGGGC TGCGCAAAAT   50

AGCAGAGCAT CACTTGAGCA AATCACCTG CAGGGG   86

( 2 ) INFORMATION FOR SEQ ID NO: 10:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 10:

ATCCGCCTGA TTAGCGATAC TGGTGGACTA GAGGGCAGCA AACGATCCTT   50

GGTTAGCGTC CACTTGAGCA AATCACCTG CAGGGG   86

( 2 ) INFORMATION FOR SEQ ID NO: 11:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 11:

ATCCGCCTGA TTAGCGATAC TGGTGCGACG AGGCTTACAC AAACGTACAC   50

GTTTCCCCGC ACTTGAGCAA AATCACCTGC AGGGG   85

( 2 ) INFORMATION FOR SEQ ID NO: 12:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 12:

ATCCGCCTGA TTAGCGATAC TTGTCGGAGC AGGGGCGTAC GAAAACTTTA    50

CAGTTCCCCC GACTTGAGCA AAATCACCTG CAGGGG    86

( 2 ) INFORMATION FOR SEQ ID NO: 13:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ATCCGCCTGA TTAGCGATAC TAGTGGAACA GGGCACGGAG AGTCAAACTT    50

TGGTTTCCCC CACTTGAGCA AAATCACCTG CAGGGG    86

( 2 ) INFORMATION FOR SEQ ID NO: 14:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 14:

ATCCGCCTGA TTAGCGATAC TGTGGGTAGG GATCGGTGGA TGCCTCGTCA    50

CTTCTAGTCC CACTTGAGCA AAATCACCTG CAGGGG    86

( 2 ) INFORMATION FOR SEQ ID NO: 15:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 15:

ATCCGCCTGA TTAGCGATAC TGGGCGCCCT AAACAAAGGG TGGTCACTTC    50

TAGTCCCAGG AACTTGAGCA AAATCACCTG CAGGGG    86

( 2 ) INFORMATION FOR SEQ ID NO: 16:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 16:

ATCCGCCTGA TTAGCGATAC TTCCGGGCTC GGGATTCGTG GTCACTTTCA    50

GTCCGGATA TAACTTGAGC AAAATCACCT GCAGGGG    87

( 2 ) INFORMATION FOR SEQ ID NO: 17:

( i ) SEQUENCE CHARACTERISTICS:
        ( A ) LENGTH: 84 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 17:

```
ATCCGCCTGA TTAGCGATAC TATGGGAGGG CGCGTTCTTC GTGGTTACTT        50
TTAGTCCCGA CTTGAGCAAA ATCACCTGCA GGGG                         84
```

( 2 ) INFORMATION FOR SEQ ID NO: 18:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 18:

```
ATCCGCCTGA TTAGCGATAC TACGGGAGGG CACGTTCTTC GTGGTTACTT        50
TTAGTCCCGA CTTGAGCAAA ATCACCTGCA GGGG                         84
```

( 2 ) INFORMATION FOR SEQ ID NO: 19:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 19:

```
ATCCGCCTGA TTAGCGATAC TGCTCGTAGG GGGCGATTCT TTCGCCGTTA        50
CTTCCAGTCC TACTTGAGCA AAATCACCTG CAGGGG                       86
```

( 2 ) INFORMATION FOR SEQ ID NO: 20:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 20:

```
ATCCGCCTGA TTAGCGATAC TGAGGCATGT TAACATGAGC ATCGTCTCAC        50
GATCCTCAGC CACTTGAGCA AAATCACCTG CAGGGG                       86
```

( 2 ) INFORMATION FOR SEQ ID NO: 21:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 21:

```
ATCCGCCTGA TTAGCGATAC TCCACAGGCT ACGGCACGTA GAGCATCACC        50
ATGATCCTGT GACTTGAGCA AAATCACCTG CAGGGG                       86
```

( 2 ) INFORMATION FOR SEQ ID NO: 22:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 22:

```
ATCCGCCTGA  TTAGCGATAC  TGCGGGCATG  GCACATGAGC  ATCTCTGATC      50
CCGCAATCCT  CACTTGAGCA  AAATCACCTG  CAGGGG                      86
```

( 2 ) INFORMATION FOR SEQ ID NO: 23:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 23:

```
ATCCGCCTGA  TTAGCGATAC  TACCGGGCTA  CTTCGTAGAG  CATCTCTGAT      50
CCCGGTGCTC  GACTTGAGCA  AAATCACCTG  CAGGGG                      86
```

( 2 ) INFORMATION FOR SEQ ID NO: 24:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 24:

```
ATCCGCCTGA  TTAGCGATAC  TAAAGGGCGA  ACGTAGGTCG  AGGCATCCAT      50
TGGATCCCTT  CACTTGAGCA  AAATCACCTG  CAGGGG                      86
```

( 2 ) INFORMATION FOR SEQ ID NO: 25:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 25:

```
ATCCGCCTGA  TTAGCGATAC  TACGGGCTCT  GTCACTGTGG  CACTAGCAAT      50
AGTCCCGTCG  CACTTGAGCA  AAATCACCTG  CAGGGG                      86
```

( 2 ) INFORMATION FOR SEQ ID NO: 26:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 26:

```
ATCCGCCTGA  TTAGCGATAC  TGGGCAGACC  TTCTGGACGA  GCATCACCTA        50

TGTGATCCCG  ACTTGAGCAA  AATCACCTGC  AGGGG                         85
```

( 2 ) INFORMATION FOR SEQ ID NO: 27:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 27:

```
ATCCGCCTGA  TTAGCGATAC  TAGAGGGGAA  GTAGGCTGCC  TGACTCGAGA        50

GAGTCCTCCC  GACTTGAGCA  AAATCACCTG  CAGGGG                        86
```

( 2 ) INFORMATION FOR SEQ ID NO: 28:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 28:

```
ATCCGCCTGA  TTAGCGATAC  TAGGGGTGCG  AAACACATAA  TCCTCGCGGA        50

TTCCCATCGC  TACTTGAGCA  AAATCACCTG  CAGGGG                        86
```

( 2 ) INFORMATION FOR SEQ ID NO: 29:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 29:

```
ATCCGCCTGA  TTAGCGATAC  TGGGGGGGCA  ATGGCGGTAC  CTCTGGTCCC        50

CTAAATACAC  TTGAGCAAAA  TCACCTGCAG  GGG                           83
```

( 2 ) INFORMATION FOR SEQ ID NO: 30:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 30:

```
ATCCGCCTGA  TTAGCGATAC  TGCGGCTCAA  AGTCCTGCTA  CCCGCAGCAC        50

ATCTGTGGTC  ACTTGAGCAA  AATCACCTGC  AGGGG                         85
```

( 2 ) INFORMATION FOR SEQ ID NO: 31:

( i ) SEQUENCE CHARACTERISTICS:
        ( A ) LENGTH: 86 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO: 31:

```
ATCCGCCTGA TTAGCGATAC TTTGGGCGTG AATGTCCACG GGTACCTCCG        50
GTCCCAAAGA GACTTGAGCA AAATCACCTG CAGGGG                       86
```

( 2 ) INFORMATION FOR SEQ ID NO: 32:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 32:

```
ATCCGCCTGA TTAGCGATAC TTCCGCGCAA GTCCCTGGTA AAGGGCAGCC        50
CTAACTGGTC ACTTGAGCAA AATCACCTGC AGGG                         85
```

( 2 ) INFORMATION FOR SEQ ID NO: 33:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 33:

```
ATCCGCCTGA TTAGCGATAC TCAAGTTCCC CACAAGACTG GGGCTGTTCA        50
AACCGCTAGT AACTTGAGCA AAATCACCTG CAGGGG                       86
```

( 2 ) INFORMATION FOR SEQ ID NO: 34:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 34:

```
ATCCGCCTGA TTAGCGATAC TCAAGTAGGG CGCGACACAC GTCCGGGCAC        50
CTAAGGTCCC AACTTGAGCA AAATCACCTG CAGGGG                       86
```

( 2 ) INFORMATION FOR SEQ ID NO: 35:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 35:

```
ATCCGCCTGA TTAGCGATAC TAAAGTCGTG CAGGGTCCCC TGGAAGCATC        50
TCCGATCCCA GACTTGAGCA AAATCACCTG CAGGGG                       86
```

( 2 ) INFORMATION FOR SEQ ID NO: 36:

( i ) SEQUENCE CHARACTERISTICS:
  ( A ) LENGTH: 96 base pairs
  ( B ) TYPE: nucleic acid
  ( C ) STRANDEDNESS: single
  ( D ) TOPOLOGY: linear ( i i ) MOLECULE TYPE: RNA ( x i ) SEQUENCE DESCRIPTION: SEQ ID NO: 36:

GGGAGACAAG AAUAACGCUC AANNNNNNNN NNNNNNNNNN NNNNNNNNNN  50

NNNNNNNNNN NNNNNNNNNN NNUUCGACAG GAGGCUCACA ACAGGC  96

( 2 ) INFORMATION FOR SEQ ID NO: 37:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 37:

TAATACGACT CACTATAGGG AGACAAGAAT AACGCTCAA  39

( 2 ) INFORMATION FOR SEQ ID NO: 38:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 38:

GCCTGTTGTG AGCCTCCTGT CGAA  24

( 2 ) INFORMATION FOR SEQ ID NO: 39:

( i ) SEQUENCE CHARACTERISTICS:
    ( A ) LENGTH: 93 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F
           modified ( x i ) SEQUENCE DESCRIPTION: SEQ ID NO: 39:

GGGAGACAAG AAUAACGCUC AACGGUGGCA UUUCUUCACU UCCUUCUCGC  50

UUUCUCGCGU UGGGCNCGAU UCGACAGGAG GCUCACAACA GGC  93

( 2 ) INFORMATION FOR SEQ ID NO: 40:

( i ) SEQUENCE CHARACTERISTICS:
    ( A ) LENGTH: 91 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F
           modified ( x i ) SEQUENCE DESCRIPTION: SEQ ID NO: 40:

GGGAGACAAG AAUAACGCUC AACCAACCUU CUGUCGGCGU UGCUUUUUGG      50

ACGGCACUCA GGCUCCAUUC GACAGGAGGC UCACAACAGG C      91

( 2 ) INFORMATION FOR SEQ ID NO:41 :

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 41:

GGGAGACAAG AAUAACGCUC AAUCGAUCGG UUGUGUGCCG GACAGCCUUA      50

ACCAGGGCUG GGACCGAGGC CUUCGACAGG AGGCUCACAA CAGGC      95

( 2 ) INFORMATION FOR SEQ ID NO: 42:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 42:

GGGAGACAAG AAUAACGCUC AACUGAGUAG GGGAGGAAGU UGAAUCAGUU      50

GUGGCGCCUC UCAUUCGCUU CGACAGGAGG CUCACAACAG GC      92

( 2 ) INFORMATION FOR SEQ ID NO: 43:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 43:

GGGAGACAAG AAUAACGCUC AACAGCACUU UCGCUUUUCA UCAUUUUUUC      50

UUUCCACUGU UGGGCGCGGA AUUCGACAGG AGGCUCACAA CAGGC      95

( 2 ) INFORMATION FOR SEQ ID NO: 44:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All pyrimidines are 2'-F
        modified ( x i ) SEQUENCE DESCRIPTION: SEQ ID NO: 44:

GGGAGACAAG AAUAACGCUC AAUCAGUGCU GGCGUCAUGU CUCGAUGGGG    50

AUUUUUCUUC AGCACUUUGC CAUUCGACAG GAGGCUCACA ACAGGC    96

( 2 ) INFORMATION FOR SEQ ID NO: 45:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 45:

GGGAGACAAG AAUAACGCUC AAUCUACUUU CCAUUUCUCU UUUCUUCUCA    50

CGAGCGGGUU UCCAGUGAAC CAUUCGACAG GAGGCUCACA ACAGGC    96

( 2 ) INFORMATION FOR SEQ ID NO: 46:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 46:

GGGAGACAAG AAUAACGCUC AACGAUAGUG ACUACGAUGA CGAAGGCCGC    50

GGGUUGGAUG CCCGCAUUGA UUCGACAGGA GGCUCACAAC AGGC    94

( 2 ) INFORMATION FOR SEQ ID NO: 47:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 47:

GGGAGACAAG AAUAACGCUC AAGUCGAUAC UGGCGACUUG CUCCAUUGGC    50

CGAUUAACGA UUCGGUCAGU UCGACAGGAG GCUCACAACA GGC    93

( 2 ) INFORMATION FOR SEQ ID NO: 48:

( i ) SEQUENCE CHARACTERISTICS:
        ( A ) LENGTH: 95 base pairs
        ( B ) TYPE: nucleic acid (C) STRANDEDNESS: single
(D) TOPOLOGY: linear (ii) MOLECULE TYPE: RNA (ix) FEATURE:
　　(D) OTHER INFORMATION: All pyrimidines are 2'-F
　　　modified (xi) SEQUENCE DESCRIPTION: SEQ ID NO: 48:

| GGGAGACAAG | AAUAACGCUC | AAGUGCAAAC | UUAACCCGGG | AACCGCGCGU | 50 |
| UUCGAUCGAC | UUUCCUUUCC | AUUCGACAGG | AGGCUCACAA | CAGGC | 95 |

(2) INFORMATION FOR SEQ ID NO: 49:

(i) SEQUENCE CHARACTERISTICS:
　　(A) LENGTH: 96 base pairs
　　(B) TYPE: nucleic acid
　　(C) STRANDEDNESS: single
　　(D) TOPOLOGY: linear (ii) MOLECULE TYPE: RNA (ix) FEATURE:
　　(D) OTHER INFORMATION: All pyrimidines are 2'-F
　　　modified (xi) SEQUENCE DESCRIPTION: SEQ ID NO: 49:

| GGGAGACAAG | AAUAACGCUC | AAAUUCCGCG | UUCGAUUAA | UCCUGUGCUC | 50 |
| GGAAAUCGGU | AGCCAUAGUG | CAUUCGACAG | GAGGCUCACA | ACAGGC | 96 |

(2) INFORMATION FOR SEQ ID NO: 50:

(i) SEQUENCE CHARACTERISTICS:
　　(A) LENGTH: 94 base pairs
　　(B) TYPE: nucleic acid
　　(C) STRANDEDNESS: single
　　(D) TOPOLOGY: linear (ii) MOLECULE TYPE: RNA (ix) FEATURE:
　　(D) OTHER INFORMATION: All pyrimidines are 2'-F
　　　modified (xi) SEQUENCE DESCRIPTION: SEQ ID NO: 50:

| GGGAGACAAG | AAUAACGCUC | AACGAACGAG | GAGGGAGUGG | CAAGGGAUGG | 50 |
| UUGGAUAGGC | UCUACGCUCA | UUCGACAGGA | GGCUCACAAC | AGGC | 94 |

(2) INFORMATION FOR SEQ ID NO: 51:

(i) SEQUENCE CHARACTERISTICS:
　　(A) LENGTH: 94 base pairs
　　(B) TYPE: nucleic acid
　　(C) STRANDEDNESS: single
　　(D) TOPOLOGY: linear (ii) MOLECULE TYPE: RNA (ix) FEATURE:
　　(D) OTHER INFORMATION: All pyrimidines are 2'-F
　　　modified (xi) SEQUENCE DESCRIPTION: SEQ ID NO: 51:

| GGGAGACAAG | AAUAACGCUC | AAGCGAAACU | GGCGACUUGC | UCCAUUGGCC | 50 |
| GAUAUAACGA | UUCGGUUCAU | UUCGACAGGA | GGCUCACAAC | AGGC | 94 |

(2) INFORMATION FOR SEQ ID NO: 52:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F modified ( x i ) SEQUENCE DESCRIPTION: SEQ ID NO: 52:

GGGAGACAAG AAUAACGCUC AACGAACGAG GAGGGAGUCG CAAGGGAUGG     50
UUGGAUAGGC UCUACGCUCA AUUCGACAGG AGGCUCACAA CAGGC          95

( 2 ) INFORMATION FOR SEQ ID NO: 53:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F modified ( x i ) SEQUENCE DESCRIPTION: SEQ ID NO: 53:

GGGAGACAAG AAUAACGCUC AACGAGAAGU GACUACGAUG ACGAAGGCCG     50
CGGGUUGAAU CCCUCAUUGA UUCGACAGGA GGCUCACAAC AGGC           94

( 2 ) INFORMATION FOR SEQ ID NO: 54:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F modified ( x i ) SEQUENCE DESCRIPTION: SEQ ID NO: 54:

GGGAGACAAG AAUAACGCUC AAAAGCAACG AGACCUGACG CCUGAUGUGA     50
CUGUGCUUGC ACCCGAUUCU GUUCGACAGG AGGCUCACAA CAGGC          95

( 2 ) INFORMATION FOR SEQ ID NO: 55:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F modified ( x i ) SEQUENCE DESCRIPTION: SEQ ID NO: 55:

GGGAGACAAG AAUAACGCUC AAGUGAUUCU CAUUCUCAAU GCUUUCUCAC     50

```
AACUUUUUCC ACUUCAGCGU GAUUCGACAG GAGGCUCACA ACAGGC                96
```

( 2 ) INFORMATION FOR SEQ ID NO: 56:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 56:

```
GGGAGACAAG AAUAACGCUC AAAAGCAACG AGACUCGACG CCUGAUGUGA          50

CUGUGCUUGC ACCCGAUUCU UUCGACAGGA GGCUCACAAC AGGC                94
```

( 2 ) INFORMATION FOR SEQ ID NO: 57:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 57:

```
GGGAGACAAG AAUAACGCUC AAUCGAUCGG UUGUGUGCCG GACAGCUUUG          50

ACCAUGAGCU GGGACCGAGG CCUUCGACAG GAGGCUCACA ACAGGC              96
```

( 2 ) INFORMATION FOR SEQ ID NO: 58:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 58:

```
GGGAGACAAG AAUAACGCUC AANGACGNGU GGACCUGACU AAUCGACUGA          50

UCAAAGAUCC CGCCCAGAUG GGUUCGACAG GAGGCUCACA ACAGGC              96
```

( 2 ) INFORMATION FOR SEQ ID NO: 59:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 59:

GGGAGACAAG AAUAACGCUC AACACUGCGA CUUGCAGAAG CCUUGUGUGG         50

CGGUACCCCC UUUGGCCUCG UUCGACAGGA GGCUCACAAC AGGC               94

( 2 ) INFORMATION FOR SEQ ID NO: 60:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 60:

GGGAGACAAG AAUAACGCUC AAGGUGGCAU UUCUUCAUUU UCCUUCUCGC         50

UUUCUCCGCC GUUGGGCGCG UUCGACAGGA GGCUCACAAC AGGC               94

( 2 ) INFORMATION FOR SEQ ID NO: 61:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 61:

GGGAGACAAG AAUAACGCUC AACCUGAGUA GGGGGGAAAG UUGAAUCAGU         50

UGUGGCGCUC UACUCAUUCG CCUUCGACAG GAGGCUCACA ACAGGC             96

( 2 ) INFORMATION FOR SEQ ID NO: 62:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 62:

GGGAGACAAG AAUAACGCUC AAGUCGAAAC UGGCGACUUG CUCCAUUGGC         50

CGAUAUAACG AUUCGGUUCA UUCGACAGGA GGCUCACAAC AGGC               94

( 2 ) INFORMATION FOR SEQ ID NO: 63:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
      ( D ) OTHER INFORMATION: All pyrimidines are 2'-F
            modified ( x i ) SEQUENCE DESCRIPTION: SEQ ID NO: 63:

GGGAGACAAG AAUAACGCUC AAGCGAUACU GGCGACUUGC UCCAUUGGCC    50

GAUAUAACGA UUCGGCUCAG UUCGACAGGA GGCUCACAAC AGGC          94

( 2 ) INFORMATION FOR SEQ ID NO: 64:

( i ) SEQUENCE CHARACTERISTICS:
            ( A ) LENGTH: 96 base pairs
            ( B ) TYPE: nucleic acid
            ( C ) STRANDEDNESS: single
            ( D ) TOPOLOGY: linear ( i i ) MOLECULE TYPE: RNA ( i x ) FEATURE:
            ( D ) OTHER INFORMATION: All pyrimidines are 2'-F
                  modified ( x i ) SEQUENCE DESCRIPTION: SEQ ID NO: 64:

GGGAGACAAG AAUAACGCUC AAACGUGGGG CACAGGACCG AGAGUCCCUC    50

CGGCAAUAGC CGCUACCCCA CCUUCGACAG GAGGCUCACA ACAGGC        96

( 2 ) INFORMATION FOR SEQ ID NO: 65:

( i ) SEQUENCE CHARACTERISTICS:
            ( A ) LENGTH: 98 base pairs
            ( B ) TYPE: nucleic acid
            ( C ) STRANDEDNESS: single
            ( D ) TOPOLOGY: linear ( i i ) MOLECULE TYPE: RNA ( i x ) FEATURE:
            ( D ) OTHER INFORMATION: All pyrimidines are 2'-F
                  modified ( x i ) SEQUENCE DESCRIPTION: SEQ ID NO: 65:

GGGAGACAAG AAUAACGCUC AACACAGCCU NANAGGGGGG AAGUUGAAUC    50

AGUUGUGGCG CUCUACUCAU UCGCUUCGAC AGGAGGCUCA CAACAGGC      98

( 2 ) INFORMATION FOR SEQ ID NO: 66:

( i ) SEQUENCE CHARACTERISTICS:
            ( A ) LENGTH: 94 base pairs
            ( B ) TYPE: nucleic acid
            ( C ) STRANDEDNESS: single
            ( D ) TOPOLOGY: linear ( i i ) MOLECULE TYPE: RNA ( i x ) FEATURE:
            ( D ) OTHER INFORMATION: All pyrimidines are 2'-F
                  modified ( x i ) SEQUENCE DESCRIPTION: SEQ ID NO: 66:

GGGAGACAAG AAUAACGCUC AAANGGGNUA UGGUGACUUG CUCCAUUGGC    50

CGAUAUAACG AUUCGGUCAG UUCGACAGGA GGCUCACAAC AGGC          94

( 2 ) INFORMATION FOR SEQ ID NO: 67:

( i ) SEQUENCE CHARACTERISTICS:
            ( A ) LENGTH: 96 base pairs
            ( B ) TYPE: nucleic acid
            ( C ) STRANDEDNESS: single (D) TOPOLOGY: linear (i i) MOLECULE TYPE: RNA (i x) FEATURE:
(D) OTHER INFORMATION: All pyrimidines are 2'-F modified (x i) SEQUENCE DESCRIPTION: SEQ ID NO: 67:

| | | | | |
|---|---|---|---|---|
| GGGAGACAAG | AAUAACGCUC | AACCUGCGUA | GGGNGGGAAG | UUGAAUCAGU | 50 |
| UGUGGCGCUC | UACUCAUUCG | CCUUCGACAG | GAGGCUCACA | ACAGGC | 96 |

(2) INFORMATION FOR SEQ ID NO: 68:

(i) SEQUENCE CHARACTERISTICS:
(A) LENGTH: 94 base pairs
(B) TYPE: nucleic acid
(C) STRANDEDNESS: single
(D) TOPOLOGY: linear (i i) MOLECULE TYPE: RNA (i x) FEATURE:
(D) OTHER INFORMATION: All pyrimidines are 2'-F modified (x i) SEQUENCE DESCRIPTION: SEQ ID NO: 68:

| | | | | |
|---|---|---|---|---|
| GGGAGACAAG | AAUAACGCUC | AACGAACGAG | GAGGGAGUGG | CAAGGGAUGG | 50 |
| UUGGAUAGGC | UCUACGCUCA | UUCGACAGGA | GGCUCACAAC | AGGC | 94 |

(2) INFORMATION FOR SEQ ID NO: 69:

(i) SEQUENCE CHARACTERISTICS:
(A) LENGTH: 97 base pairs
(B) TYPE: nucleic acid
(C) STRANDEDNESS: single
(D) TOPOLOGY: linear (i i) MOLECULE TYPE: RNA (i x) FEATURE:
(D) OTHER INFORMATION: All pyrimidines are 2'-F modified (x i) SEQUENCE DESCRIPTION: SEQ ID NO: 69:

| | | | | |
|---|---|---|---|---|
| GGGAGACAAG | AAUAACGCUC | AAGUGCAAAC | UUAACCCGGG | AACCGCGCGU | 50 |
| UUCGAUUCGC | UUUCCNUAUU | CCAUUCGACA | GGAGGCUCAC | AACAGGC | 97 |

(2) INFORMATION FOR SEQ ID NO: 70:

(i) SEQUENCE CHARACTERISTICS:
(A) LENGTH: 93 base pairs
(B) TYPE: nucleic acid
(C) STRANDEDNESS: single
(D) TOPOLOGY: linear (i i) MOLECULE TYPE: RNA (i x) FEATURE:
(D) OTHER INFORMATION: All pyrimidines are 2'-F modified (x i) SEQUENCE DESCRIPTION: SEQ ID NO: 70:

| | | | | |
|---|---|---|---|---|
| GGGAGACAAG | AAUAACGCUC | AACGAACGAG | GAGGGAGUGG | CAAGGGACGG | 50 |
| UNNAUAGGCU | CUACGCUCAU | UCGACAGGAG | GCUCACAACA | GGC | 93 |

(2) INFORMATION FOR SEQ ID NO: 71:

( i ) SEQUENCE CHARACTERISTICS:
    ( A ) LENGTH: 93 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F
        modified ( x i ) SEQUENCE DESCRIPTION: SEQ ID NO: 71:

| GGGAGACAAG | AAUAACGCUC | AAUCGGUGUG | GCUCAGAAAC | UGACACGCGU | 50 |
| GAGCUUCGCA | CACAUCUGCU | UCGACAGGAG | GCUCACAACA | GGC | 93 |

( 2 ) INFORMATION FOR SEQ ID NO: 72:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F
        modified ( x i ) SEQUENCE DESCRIPTION: SEQ ID NO: 72:

| GGGAGACAAG | AAUAACGCUC | AAUAUCGCUU | UUCAUCAAUU | CCACUUUUUC | 50 |
| ACUCUNUAAC | UUGGGCGUGC | AUUCGACAGG | AGGCUCACAA | CAGGC | 95 |

( 2 ) INFORMATION FOR SEQ ID NO: 73:

( i ) SEQUENCE CHARACTERISTICS:
    ( A ) LENGTH: 96 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F
        modified ( x i ) SEQUENCE DESCRIPTION: SEQ ID NO: 73:

| GGGAGACAAG | AAUAACGCUC | AAGUGCAAAC | UUAACCCGGG | AACCGCGCGU | 50 |
| UUCGAUCCUG | CAUCCUUUUU | CCUUCGACAG | GAGGCUCACA | ACAGGC | 96 |

( 2 ) INFORMATION FOR SEQ ID NO: 74:

( i ) SEQUENCE CHARACTERISTICS:
    ( A ) LENGTH: 93 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F
        modified ( x i ) SEQUENCE DESCRIPTION: SEQ ID NO: 74:

| GGGAGACAAG | AAUAACGCUC | AAUCGNUCGG | UUGUGUGCCG | GCAGCUUUGU | 50 |
| CCAGCGUUGG | GCCGAGGCCU | UCGACAGGAG | GCUCACAACA | GGC | 93 |

( 2 ) INFORMATION FOR SEQ ID NO: 75:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F modified ( x i ) SEQUENCE DESCRIPTION: SEQ ID NO: 75:

| GGGAGACAAG | AAUAACGCUC | AAGUACCCA | UCUCAUCUUU | UCCUUUCCUU | 50 |
| UCUUCAAGGC | ACAUUGAGGG | UUUCGACAGG | AGGCUCACAA | CAGGC | 95 |

( 2 ) INFORMATION FOR SEQ ID NO: 76:

( i ) SEQUENCE CHARACTERISTICS:
    ( A ) LENGTH: 97 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F modified ( x i ) SEQUENCE DESCRIPTION: SEQ ID NO: 76:

| GGGAGACAAG | AAUAACGCUC | AACCUGAGUA | GGGGGGGAAG | UUGAACCAGU | 50 |
| UGUGGCNGCC | UACUCAUUCN | CCAUUCGACA | GGAGGCUCAC | AACAGGC | 97 |

( 2 ) INFORMATION FOR SEQ ID NO: 77:

( i ) SEQUENCE CHARACTERISTICS:
    ( A ) LENGTH: 94 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F modified ( x i ) SEQUENCE DESCRIPTION: SEQ ID NO: 77:

| GGGAGACAAG | AAUAACGCUC | AACCNNCCUN | CUGUCGGCGC | UUGUCUUUUU | 50 |
| GGACGGGCAA | CCCAGGGCUC | UUCGACAGGA | GGCUCACAAC | AGGC | 94 |

( 2 ) INFORMATION FOR SEQ ID NO: 78:

( i ) SEQUENCE CHARACTERISTICS:
    ( A ) LENGTH: 96 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All pyrimidines are 2'-F modified ( x i ) SEQUENCE DESCRIPTION: SEQ ID NO: 78:

```
GGGAGACAAG  AAUAACGCUC  AACCAACCUN  CUGUCGGCGC  UUGUCUUUUU        50

GGACGAGCAA  CUCAAGGCUC  GUUUCGACAG  GAGGCUCACA  ACAGGC            96
```

( 2 ) INFORMATION FOR SEQ ID NO: 79:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 79:

```
GGGAGACAAG  AAUAACGCUC  AACCAGCGCA  GAUCCCGGGC  UGAAGUGACU        50

GCCGGCAACG  GCCGCUCCAU  UCGACAGGAG  GCUCACAACA  GGC               93
```

( 2 ) INFORMATION FOR SEQ ID NO: 80:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 80:

```
GGGAGACAAG  AAUAACGCUC  AAUUCCCGUA  ACAACUUUUC  AUUUCACUU         50

UUCAUCCAAC  CAGUGAGCAG  CAUUCGACAG  GAGGCUCACA  ACAGGC            96
```

( 2 ) INFORMATION FOR SEQ ID NO: 81:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 81:

```
GGGAGACAAG  AAUAACGCUC  AAUAUCGCUU  UCAUCAAAUU  CCACUCCUUC        50

ACUUCUUUAA  CUUGGGCGUG  CAUUCGACAG  GAGGCUCACA  ACAGGC            96
```

( 2 ) INFORMATION FOR SEQ ID NO: 82:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:

-continued ( D ) OTHER INFORMATION: N at positions 1 and 25
                    is any base pair.

( i x ) FEATURE:
          ( D ) OTHER INFORMATION: N at positions 6 and 11
                    is any base pair.

( i x ) FEATURE:
          ( D ) OTHER INFORMATION: N at positions 7 and 10
                    is any base pair.

( i x ) FEATURE:
          ( D ) OTHER INFORMATION: N at positions 8 and 9 is
                    any base pair.

( x i ) SEQUENCE DESCRIPTION: SEQ ID NO: 82:

NGGGCNNNNN NGRKYAYYRR TCCCN                                      25

( 2 ) INFORMATION FOR SEQ ID NO: 83:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( i i ) MOLECULE TYPE: DNA ( i x ) FEATURE:
          ( D ) OTHER INFORMATION: Nucleotide 38 is an
                    inverted orientation T (3 -3 linked)

( x i ) SEQUENCE DESCRIPTION: SEQ ID NO: 83:

TGGGAGGGCG CGTTCTTCGT GGTTACTTTT AGTCCCGT                         38

( 2 ) INFORMATION FOR SEQ ID NO: 84:

( i ) SEQUENCE CHARACTERISTICS:
          ( A ) LENGTH: 40 base pairs
          ( B ) TYPE: nucleic acid
          ( C ) STRANDEDNESS: single
          ( D ) TOPOLOGY: linear ( i i ) MOLECULE TYPE: DNA ( i x ) FEATURE:
          ( D ) OTHER INFORMATION: Nucleotide 40 is an
                    inverted orientation T (3 -3 linked)

( x i ) SEQUENCE DESCRIPTION: SEQ ID NO: 84:

CACAGGCTAC GGCACGTAGA GCATCACCAT GATCCTGTGT                       40

( 2 ) INFORMATION FOR SEQ ID NO: 85:

( i ) SEQUENCE CHARACTERISTICS:
          ( A ) LENGTH: 45 base pairs
          ( B ) TYPE: nucleic acid
          ( C ) STRANDEDNESS: single
          ( D ) TOPOLOGY: linear ( i i ) MOLECULE TYPE: DNA ( i x ) FEATURE:
          ( D ) OTHER INFORMATION: Nucleotide 45 is an
                    inverted orientation T (3 -3 linked)

( x i ) SEQUENCE DESCRIPTION: SEQ ID NO: 85:

TACTCAGGGC ACTGCAAGCA ATTGTGGTCC CAATGGGCTG AGTAT                 45

( 2 ) INFORMATION FOR SEQ ID NO: 86:

( i ) SEQUENCE CHARACTERISTICS:

(A) LENGTH: 36 base pairs
(B) TYPE: nucleic acid
(C) STRANDEDNESS: single
(D) TOPOLOGY: linear (i i) MOLECULE TYPE: DNA (i x) FEATURE:
(D) OTHER INFORMATION: C at positions 8, 11, 25 and 26 is 2 O-methyl-2 -deoxycytidine.

(i x) FEATURE:
(D) OTHER INFORMATION: G at positions 9, 10, 17, 19 and 35 is 2 -O-methyl-2 -deoxyguanosine.

(i x) FEATURE:
(D) OTHER INFORMATION: A at positions 12, 24 and 27 is 2 - O-methyl-2 -deoxyadenosine.

(i x) FEATURE:
(D) OTHER INFORMATION: U at position 34 is 2 -O-methyl- 2 -deoxyuridine.

(i x) FEATURE:
(D) OTHER INFORMATION: U at positions 6 and 22 is 2 -fluoro-2 - deoxyuridine.

(i x) FEATURE:
(D) OTHER INFORMATION: C at positions 23, 32 and 33 is 2 - fluoro-2 -deoxycytidine.

(i x) FEATURE:
(D) OTHER INFORMATION: Nucleotide 36 is an inverted orientation T (3 -3 linked).

(x i) SEQUENCE DESCRIPTION: SEQ ID NO: 86:

CAGGCUACGG CACGTAGAGC AUCACCATGA TCCUGT                36

(2) INFORMATION FOR SEQ ID NO: 87:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: DNA (i x) FEATURE:
(D) OTHER INFORMATION: C at position 8 is 2 - O-methyl-2 - deoxycytidine.

(i x) FEATURE:
(D) OTHER INFORMATION: G at positions 9, 17 and 31 is 2 - O-methyl-2 -deoxyguanosine.

(i x) FEATURE:
(D) OTHER INFORMATION: A at position 22 is 2 -O-methyl- 2 -deoxyadenine.

(i x) FEATURE:
(D) OTHER INFORMATION: U at position 30 is 2 - O-methyl-2 - deoxyuridine.

(i x) FEATURE:
(D) OTHER INFORMATION: U at positions 6 and 20 is 2 - fluoro-2 -deoxyuridine.

(i x) FEATURE:
(D) OTHER INFORMATION: C at positions 21, 28 and 29 is 2 - fluoro-2 -deoxycytidine.

(i x) FEATURE:
(D) OTHER INFORMATION: N at positions 10 and 23 is pentaethylene glycol phosphoramidite spacer.

(i x) FEATURE:

(D) OTHER INFORMATION: Nucleotide 32 is an
inverted orientation T (3 -3 linked)

(x i) SEQUENCE DESCRIPTION: SEQ ID NO: 87:

CAGGCUACGN CGTAGAGCAU CANTGATCCU GT                32

(2) INFORMATION FOR SEQ ID NO: 88:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: Nucleotide 39 is an
    inverted orientation T (3 -3 linked)

(x i) SEQUENCE DESCRIPTION: SEQ ID NO: 88:

CAGTCCGTGG TAGGGCAGGT TGGGGTGACT TCGTGGAAT           39

(2) INFORMATION FOR SEQ ID NO: 89:

(i) SEQUENCE CHARACTERISTICS:
    (A) LENGTH: 37 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: T at positions 13, 14,
    16 and 17 is substituted with IdU.

(x i) SEQUENCE DESCRIPTION: SEQ ID NO: 89:

TGGGAGGGCG CGTTCTTCGT GGTTACTTTT AGTCCCG             37

(2) INFORMATION FOR SEQ ID NO: 90:

(i) SEQUENCE CHARACTERISTICS:
    (A) LENGTH: 37 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: T at position 20 is
    substituted with IdU.

(x i) SEQUENCE DESCRIPTION: SEQ ID NO: 90:

TGGGAGGGCG CGTTCTTCGT GGTTACTTTT AGTCCCG             37

(2) INFORMATION FOR SEQ ID NO: 91:

(i) SEQUENCE CHARACTERISTICS:
    (A) LENGTH: 37 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: T at position 23 is
    substituted with IdU.

(x i) SEQUENCE DESCRIPTION: SEQ ID NO: 91:

TGGGAGGGCG CGTTCTTCGT GGTTACTTTT AGTCCCG    37

( 2 ) INFORMATION FOR SEQ ID NO: 92:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: T at position 24 is
        substituted with IdU.

( x i ) SEQUENCE DESCRIPTION: SEQ ID NO: 92:

TGGGAGGGCG CGTTCTTCGT GGTTACTTTT AGTCCCG    37

( 2 ) INFORMATION FOR SEQ ID NO: 93:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: T at position 27 is
        substituted with IdU.

( x i ) SEQUENCE DESCRIPTION: SEQ ID NO: 93:

TGGGAGGGCG CGTTCTTCGT GGTTACTTTT AGTCCCG    37

( 2 ) INFORMATION FOR SEQ ID NO: 94:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: T at positions 28-30 is
        substituted with IdU.

( x i ) SEQUENCE DESCRIPTION: SEQ ID NO: 94:

TGGGAGGGCG CGTTCTTCGT GGTTACTTTT AGTCCCG    37

( 2 ) INFORMATION FOR SEQ ID NO: 95:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: T at position 33 is
        substituted with IdU.

( x i ) SEQUENCE DESCRIPTION: SEQ ID NO: 95:

TGGGAGGGCG CGTTCTTCGT GGTTACTTTT AGTCCCG    37

( 2 ) INFORMATION FOR SEQ ID NO: 96:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: Peptide ( i x ) FEATURE:
      ( D ) OTHER INFORMATION: Xaa at position 5 is a
         modified amino acid that could not be identified.

( x i ) SEQUENCE DESCRIPTION: SEQ ID NO: 96:

Lys  Lys  Pro  Ile  Xaa  Lys  Lys
                    5